US012761065B2

(12) United States Patent
Fowler et al.

(10) Patent No.: US 12,761,065 B2
(45) Date of Patent: *Oct. 13, 2026

(54) TEST METHOD DEVELOPMENT FOR FLOW RATE IDENTIFICATION OF OCCLUDING SMALL PARTICULATES IN MICROLUMENS

(71) Applicant: INNOVATIVE HEALTH, Scottsdale, AZ (US)

(72) Inventors: Aaron J. Fowler, Mesa, AZ (US); Blessan Joseph, Chandler, AZ (US); Rafal Chudzik, Peoria, AZ (US)

(73) Assignee: INNOVATIVE HEALTH, Scottsdale, AZ (US)

( * ) Notice: Subject to any disclaimer, the term of this patent is extended or adjusted under 35 U.S.C. 154(b) by 135 days.

This patent is subject to a terminal disclaimer.

(21) Appl. No.: 17/932,006

(22) Filed: Sep. 14, 2022

(65) Prior Publication Data

US 2023/0152135 A1 May 18, 2023

Related U.S. Application Data

(63) Continuation-in-part of application No. 17/530,285, filed as application No. PCT/US2020/034592 on May 26, 2020, now Pat. No. 12,025,483.

(Continued)

(51) Int. Cl.
*G01F 25/10* (2022.01)
*A61M 5/168* (2006.01)

(Continued)

(52) U.S. Cl.
CPC ......... *G01F 25/10* (2022.01); *A61M 5/16831* (2013.01); *G01F 1/76* (2013.01);

(Continued)

(58) Field of Classification Search
CPC .. G01F 1/76; G01F 25/10; G01F 1/74; A61M 5/16831; A61M 2005/16863;

(Continued)

(56) References Cited

U.S. PATENT DOCUMENTS

| | | |
|---|---|---|
| 3,505,843 A | 4/1970 | Kelsay |
| 4,648,270 A | 3/1987 | Johnson et al. |

(Continued)

FOREIGN PATENT DOCUMENTS

| | | |
|---|---|---|
| GB | 2 367 594 A | 4/2002 |
| WO | 2006/076119 A2 | 7/2006 |

OTHER PUBLICATIONS

International Search Report of PCT/US20/34592 dated Jun. 30, 2020.

(Continued)

*Primary Examiner* — Benjamin R Schmitt
(74) *Attorney, Agent, or Firm* — POLSINELLI PC

(57) ABSTRACT

Method and systems for determining acceptance criteria for identification of occluding particles in a lumen of a device are provided. The methods and systems can be used in methods of identifying an occluded device in an inspection method. The method can include obtaining or having obtained a flow measurement for the device to be inspected and comparing the flow measurement in the device to acceptance criteria for a representative device.

8 Claims, 32 Drawing Sheets

Related U.S. Application Data

(60) Provisional application No. 62/852,498, filed on May 24, 2019.

(51) Int. Cl.

| | |
|---|---|
| ***G01F 1/76*** | (2006.01) |
| ***G01F 1/84*** | (2006.01) |
| ***G01F 15/02*** | (2006.01) |
| *A61B 17/00* | (2006.01) |
| *G01F 1/74* | (2006.01) |

(52) U.S. Cl.

CPC ................ *G01F 1/84* (2013.01); *G01F 15/02* (2013.01); *A61B 2017/00725* (2013.01); *A61M 2005/16863* (2013.01); *A61M 2205/70* (2013.01); *G01F 1/74* (2013.01)

(58) Field of Classification Search

CPC ..... A61M 2205/70; A61B 2017/00725; A61B 2560/06

See application file for complete search history.

(56) References Cited

U.S. PATENT DOCUMENTS

| | | | |
|---|---|---|---|
| 5,503,036 | A | 4/1996 | Nguyen et al. |
| 2006/0010964 | A1 | 1/2006 | Sparks et al. |
| 2009/0078047 | A1 | 3/2009 | Dam |
| 2012/0060626 | A1 | 3/2012 | Zhu et al. |
| 2014/0378352 | A1 | 12/2014 | Daridon |
| 2015/0057538 | A1 | 2/2015 | Cragg et al. |
| 2017/0173262 | A1 | 6/2017 | Veltz |

OTHER PUBLICATIONS

Non-Final Office Action of co-pending U.S. Appl. No. 17/530,285 dated Mar. 6, 2024.

Extended European Search of Regional Phase EP 20815119.1 dated May 25, 2023.

TEST METHOD DEVELOPMENT FOR FLOW RATE IDENTIFICATION OF OCCLUDING SMALL PARTICULATES IN MICROLUMENS

CROSS-REFERENCE TO RELATED APPLICATIONS

This application is a continuation-in-part of U.S. application Ser. No. 17/530,285 filed Nov. 18, 2021, which is a National Stage application of International Application No. PCT/US20/34592, filed May 26, 2020, and published as WO 2020/243114 on Dec. 3, 2020, which claims the benefit of U.S. Provisional Patent Application No. 62/852,498 filed May 24, 2019, the entire disclosures of all of which are incorporated herein by reference.

FIELD OF THE INVENTION

The present disclosure provides methods and systems for determining acceptance criteria for identification of occluding particles in a lumen of a device.

BACKGROUND OF THE INVENTION

The risk of patient injury induced by excessive loads of injected particles during hospital stays has long been understood, and reducing their occurrence is a primary goal of manufacturers and practitioners alike. A contributing factor to these complications results from potentially embolic particulates either on, in, or created by, a device, fluid, or other object introduced into the patient. The consequences of particles delivered into the bloodstream have long been understood. With an elementary understanding of anatomy, concern arises that the devices placed within cardiac chambers could release potentially embolic particulates. Those discharged into the right side of the heart could occlude pulmonary arterioles (average diameter <300 micron) if large enough, potentially resulting in a pulmonary embolism (PE). Left-sided studies could direct emboli to the brain, potentially resulting in a CVA. Occlusion of penetrating arterioles (average diameter <100 micron) is of greatest concern, inducing more traumatic neuropathy. While the occurrence of these events is highly unlikely (<0.2% of procedures), and not conclusively attributable to the devices used during a study, preventing them further has led to increased scrutiny of the manufacture of anything intended to be positioned in a patient.

Therefore, there is a need for testing methods and systems capable of identifying occluding particles within lumens of medical devices.

SUMMARY OF THE INVENTION

One aspect of the instant disclosure comprises a method of detecting a change in a lumen property of a lumen device. The method comprises obtaining or having obtained a mass flow measurement for the device to be inspected; and comparing the mass flow measurement in the device to acceptance criteria obtained for a representative device. The property of the device is determined to be changed if a mass flow measurement for the device is significantly different from the acceptance criteria, and the property of the device is determined to be unchanged if a mass flow measurement for the device is significantly equal to the acceptance criteria. The representative device can be an unused originally manufactured device (OM), a used OM device, an unused reprocessed device, or a used reprocessed device.

The method can further comprise determining the acceptance criteria of the representative device. In some aspects, the acceptance criteria is determined using a method comprising the steps of (a) obtaining or having obtained a mass flow measurement for a representative device occluded with a defined number of one or more occluding particles; and (b) calculating an upper test limit mass flow rate for the occluded representative device. The upper test limit mass flow rate is the acceptance criteria, and an inspected device is determined to be occluded if a mass flow measurement for the inspected device is equal to or lower than the acceptance criteria, and the inspected device is determined to be unoccluded if the mass flow measurement in the inspected device is higher than the acceptance criteria.

The change in the lumen property can comprise a change in dimensions of the lumen, a change in material of the lumen, a change in device-specific parts attached along the lumen, or any combination thereof. In some aspects, the change in material of the lumen comprises a change in material used to manufacture of the lumen by an original manufacturer, a change in material caused by intended alteration of the device, a defect caused during manufacture, a defect caused during shipping and handling of the device, a defect caused during use of the device, a change in physical characteristics of a lumen resulting from use of the device, or any combination thereof. In other aspects, the change in the dimensions of the lumen comprises an occlusion in the lumen, a change in an inner diameter and shape, tube curvature, tube length, a damaged lumen, a manufacturing defect, a new coating, a chipped coating. In additional aspects, the change in a property of the device occurred before manufacture, during manufacture, during shipping and handling, during use, after use but before re-processing, during reprocessing, after reprocessing or any combination thereof.

Another aspect of the instant disclosure encompasses a quality control method of accepting or rejecting a lumen device before use. The method comprises obtaining or having obtained a mass flow measurement for a manufactured device to be inspected; and comparing the mass flow measurement to acceptance criteria determined for a representative device. The manufactured device is accepted if a mass flow measurement for the manufactured device is substantially equal to the acceptance criteria. In some aspects, the device is a original manufactured device, a reprocessed device, an altered device, or any combination thereof.

Yet another aspect of the instant disclosure encompasses a method of quantifying the level of occlusion of a lumen of a device to be inspected. The method comprises the steps of (a) measuring or having measured change in mass flow through a lumen of a representative device as a function of a change in the level of occlusion of the lumen of the representative device; (b) obtaining or having obtained a mass flow measurement for the device to be inspected; and (c) deriving the level of occlusion of the lumen of the device to be inspected using the measured change in mass flow through a lumen of the representative device. In some aspects, the level of occlusion represents the number of particles occluding the lumen, the size of particles occluding the lumen, or any combination thereof.

One aspect of the instant disclosure encompasses a method of determining the number of particles in a lumen of a device to be inspected. The method comprises the steps of (a) measuring or having measured change in mass flow through a lumen of a representative device as a function of a predetermined change in the number of particles occluding the lumen of the representative device; (b) obtaining or having obtained a mass flow measurement for the device to be inspected; and (c) deriving the number of particles occluding the lumen of the device to be inspected using the measured change in mass flow through a lumen of the representative device.

DETAILED DESCRIPTION

Figure 1:
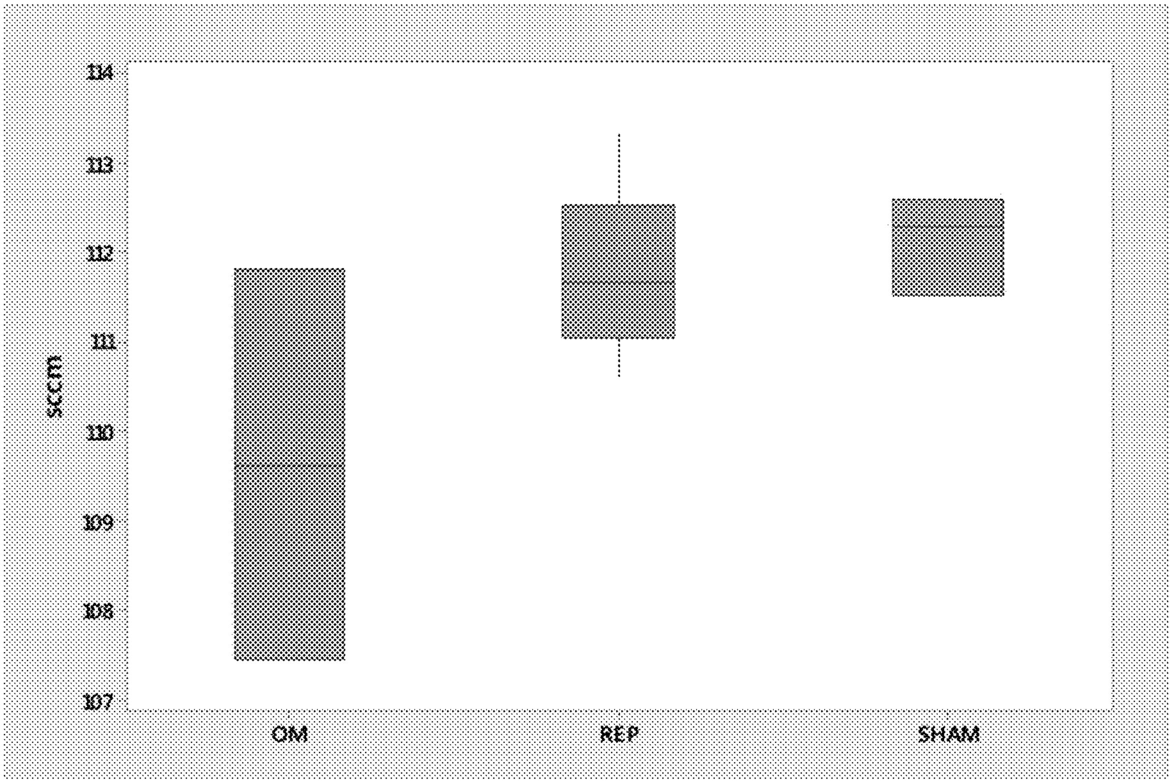
FIG. 1 depicts a plot showing mass flow readings of a device from the original manufacturer, and reprocessed untreated and sham devices treated with bead solution only. OM: original manufacturer; REP: reprocessed device untreated; SHAM: treated with bead solution only.

The present disclosure encompasses methods of determining acceptance criteria for determining if a device to be tested is occluded or unoccluded, and a method of using the acceptance criteria in methods of determining if a tested device is unoccluded. Accordingly, the present disclosure also encompasses methods of inspecting a device comprising a lumen to determine if the lumen of the inspected device is occluded by one or more occluding particles. The method can be used in an in-process method of inspecting a device to accept or pass the inspected device as unoccluded or reject the inspected device as occluded. The method can be used with any device having a lumen in any field, including the medical field. A method developed according to the present disclosure is capable of identifying a single small occluding particle within the microlumen of a medical device. Importantly, occluding particles smaller than those deemed clinically relevant can be detected using the instant methods. The ability of a test method to detect occluding particles to that resolution provides a considerable safety factor when defining acceptance criteria.

I. Method of Determining Acceptance Criteria

One aspect of the present disclosure encompasses a method of determining acceptance criteria for identification of occluding particles in a lumen of a device to be inspected. The method comprises occluding the lumen of a device representative of a device to be inspected with a defined number of particles by immobilizing the particles in the lumen of the representative device; obtaining mass or volume flow and pressure measurements of fluid in the occluded lumen of the representative device; and calculating a flow rate of the fluid in the lumen of the occluded representative device. In a method of the instant disclosure, the calculated flow rate is the acceptance criteria for determining if a device to be tested is occluded or unoccluded. An inspected device is occluded if a calculated flow rate of a fluid in the lumen of the inspected device is equal to or lower than the criteria, and the inspected device is considered unoccluded if the calculated flow rate of the fluid in the lumen of the inspected device is higher than the flow rate acceptance criteria.

A method of the instant disclosure can be used to detect as few as a single occluding particle smaller than a particle deemed clinically relevant in an inspected device with a high level of confidence. The method can also detect a wide range of particle quantities and determine the level of occlusion of an inspected device, allowing a full scale to be developed by which occlusions (partial or otherwise) could be graded. For instance, an inspection method can be developed to select unoccluded inspected devices, or inspected devices occluded to a level acceptable for the specific device or the function or procedure in which the device will be used.

(a) Device

A method of the instant disclosure can be used to determine acceptance criteria for any device comprising a lumen. As used herein, the term "lumen" refers to the internal space of a tubular structure. Non-limiting examples of devices that comprise a lumen include medical devices such as catheters and endoscopes, micropumps, microvalves, hypodermic needles, microsensors, tubing such as medical microtubing, devices in the biological field such as devices for analyzing biological materials such as proteins, DNA, cells, embryos, and chemical reagents, devices for cell culture, cell separation, nucleic acid sequencing, microfluidic devices, or devices in the electronics industry, such as in cooling channels in silicon chips.

In some aspects, the device is a medical device comprising a lumen. Non-limiting examples of medical devices that comprise lumens include medical tubing, catheters, hypodermic, transseptal, and other needles, and endoscopes.

Catheters and endoscopes are extensively used to perform an array of minimally invasive procedures. An endoscope is an illuminated optical, typically slender, and tubular instrument (a type of borescope) used to look deep into the body by way of openings such as the mouth or anus. Endoscopes use tubes which are only a few millimeters thick to transfer illumination in one direction and high-resolution images in real time in the other direction, resulting in minimally invasive surgeries. It is used to examine the internal organs like the throat or esophagus. Specialized instruments are named after their target organ. Examples include the cystoscope (bladder), nephroscope (kidney), bronchoscope (bronchus), arthroscope (joints) and colonoscope (colon), and laparoscope (abdomen or pelvis). Endoscopes can be used to visually examine and diagnose or assist in surgery such as an arthroscopy. For non-medical uses, similar instruments are called borescopes. Some endoscopes comprise working channels comprising a lumen to allow entry of medical instruments or manipulators.

A catheter is a thin tube made from medical grade materials serving a broad range of functions in medicine. Catheters can be inserted in the body to treat diseases or perform a surgical procedure. By modifying the material or adjusting the way catheters are manufactured, it is possible to tailor catheters for cardiovascular, urological, gastrointestinal, neurovascular, and ophthalmic applications. In most uses, a catheter is a thin, flexible tube ("soft" catheter) though catheters are available in varying levels of stiffness depending on the application. A catheter left inside the body, either temporarily or permanently, may be referred to as an "indwelling catheter" (for example, a peripherally inserted central catheter). A permanently inserted catheter may be referred to as a "permcath." Catheters can be inserted into a body cavity, duct, vessel, brain, skin, or adipose tissue. Functionally, catheters allow drainage and administration of fluids or gases, access by surgical instruments, and can also perform a wide variety of other tasks depending on the type of catheter.

Placement of a catheter into a particular part of the body may allow:

- Administration of fluids (i.e., heparinized saline, contrast dyes) during an electrophysiology, or related, study;
- Fluid sampling during an electrophysiology, or related, study;
- Direct blood pressure measurement during an electrophysiology, or related, study;
- Angioplasty, angiography, balloon septostomy, balloon sinuplasty, cardiac, catheter ablation;
- Draining urine from the urinary bladder as in urinary catheterization, e.g., the intermittent catheters or Foley catheter or even when the urethra is damaged as in suprapubic catheterization;
- Drainage of urine from the kidney by percutaneous (through the skin) nephrostomy;
- Drainage of fluid collections, e.g. an abdominal abscess;
- Drainage of air from around the lung (pigtail catheter);
- Administration of intravenous fluids, medication or parenteral nutrition with a peripheral venous catheter;
- Direct measurement of blood pressure in an artery or vein;
- Direct measurement of intracranial pressure;
- Administration of anesthetic medication into the epidural space, the subarachnoid space, or around a major nerve bundle such as the brachial plexus;
- Administration of oxygen, volatile anesthetic agents, and other breathing gases into the lungs using a tracheal tube;

Subcutaneous administration of insulin or other medications, with the use of an infusion set and insulin pump;

Administering drugs or fluids into a large-bore catheter positioned either in a vein near the heart or just inside the atrium;

Measuring pressures in the heart;

Inserting fertilized embryos from in vitro fertilization into the uterus;

Providing quick access to the central circulation of premature infants using an umbilical line;

Attaching catheters to various other devices;

Hemodialysis using a double or triple lumen, external catheter;

Artificial insemination.

Non-limiting examples of needles used in the medical filed include:

Abrams' needle: A biopsy needle designed to reduce the danger of introducing air into tissues; used in pleural biopsy.

Agar cutting needle: A needle with a sharpened punch end and an obturator to pick up and transfer a sample of agar media.

Aneurysm needle: A needle with a handle, used in ligating blood vessels.

Aspirating needle: A long, hollow needle for removing fluid from a cavity.

Brockenbrough needle: A curved steel transseptal needle within a

Brockenbrough transseptal catheter; used to puncture the interatrial septum.

Cataract needle: A needle used in removing a cataract.

Chiba needle: A common type of thin, flexible biopsy needle with a small-diameter needle and a stylet in the needle lumen.

Cope's needle: A blunt-ended hook-like needle with a concealed cutting edge and snare, used in biopsy of the pleura, pericardium, peritoneum, and synovium.

Deschamps' needle: A needle with the eye near the point, and a long handle attached; used in ligating deep-seated arteries.

Discission needle: A special form of cataract needle.

Emulsifying needle: A small tube with luer fittings at each end for mixing a liquid and an emulsifying agent by pushing the liquids through the tubing into opposing syringes. A simple type of static mixer.

Hagedorn's needles: Surgical needles that are flat from side to side and have a straight cutting edge near the point and a large eye.

Hasson trocar: A blunt trocar inserted into the peritoneal cavity after a celiotomy. Used for insufflation and introduction of a laparoscope.

Knife needle: A slender knife with a needle like point, used in discission of a cataract and other ophthalmic operations, as in goniotomy and goniopuncture.

Ligature needle: A slender steel needle with a long handle and an eye in its curved end, used for passing a ligature underneath an artery.

Menghini needle: A needle that does not require rotation to cut loose the tissue specimen in a biopsy of the liver. This represented a significant advance in the previously slow and hazardous methods of liver biopsy.

Reverdin's needle: A surgical needle having an eye that can be opened and closed by means of a slide.

Seldinger needle: A needle with a blunt, tapered external cannula with a sharp obturator; used for the initial percutaneous insertion characteristic of the Seldinger technique for arterial or venous access.

Silverman needle: An instrument for taking tissue specimens, consisting of an outer cannula, an obturator, and an inner split needle with longitudinal grooves in which the tissue is retained when the needle and cannula are withdrawn.

Stop needle: A needle with a shoulder that prevents it from being inserted beyond a certain distance.

Transseptal needle: A needle used to puncture the interatrial septum in transseptal catheterization.

Tuohy needle: One in which the opening at the end is angled so that a catheter exits at an angle. The end of the Tuohy needle provides controlled penetration during the administering of spinal anesthesia and placement of an epidural spinal catheter.

Veress needle: Named for Janos Veress, a German doctor. A spring-loaded needle originally used to drain ascites and evacuate fluid and air from the chest. Was later adapted to use in laparoscopy. A hollow needle consisting of a sharp trocar with a slanted end surrounding an inner cylinder with a blunt end. After the trocar is introduced into a body cavity, the blunt cylinder is advanced outward so that internal organs are not injured by the sharp edge. Used for insufflation of a body cavity, such as for pneumoperitoneum in minimally invasive surgery.

In some aspects, the medical device is a Biosense Webster PentaRay, an Abbott Advisor HD Grid, an Abbot BRK Transseptal Needle, a Baylis NRG Transseptal Needle, a Boston Scientific Orion; an Abbott Response with Lumen; a Baylis EPstar; a Phillips Eagle Eye, an *Acutus* AcQSpan, a Baylis NRG® Transseptal Needle, or a Boston Scientific INTELLAMAP ORION™ Mapping Catheter.

The diameter of a lumen in a medical device can range from about 0.1 to about 5 mm. For instance, the diameter of a lumen can range from about 0.001" to about 0.1", or from about 0.01" to about 0.05" internal diameter.

In some aspects, a medical device can further comprise a needle attached to tubing comprising the lumen. The gage of the needle can range from about 50 ga to about 5 ga, from about 40 ga to about 10 ga, or from about 30 ga to about 15 ga.

The length of a lumen of a device can range from about 1 cm to a few meters. For instance, the length of a lumen can range from about 5 cm to about 5 meters, from about 20 cm to about 4 m, from about 50 cm to about 2 m. In some aspects, the length of a lumen can range from about 50 cm to about 150 cm.

Some devices can comprise multiple lumens, each performing one or more functions. These lumens can serve as inflation ports, fluid-transfer channels, guidewire access points, or even steering lumens, among others. As such, devices can have one lumen, or can have multiple lumens. For instance, a device can have 1, 2, 3, 4, 5, 6, 7, 8, 9, or 10 or more lumens. The lumens can be a multi-lumen tube extruded or attached into a single tube or can be separately bundled inside a device.

(b) Occluding the Lumen

A method of the instant disclosure comprises isolating a defined number of one or more occluding test particles ("particles") and partially occluding the lumen of a representative device by immobilizing a defined number of particles in the lumen of the representative device. Test particles can be as described in Section I(b)(A) and methods of immobilizing the defined number of particles in the lumen of a device can be as described in Section I(b)(B).

A. Particles

Particles suitable for use in a method of the instant disclosure can be manufactured from any material suitable for generating particles of a desired size and shape, provided the particle material is compatible with a chosen method of the instant disclosure, including compatibility with a chosen method of isolating and immobilizing the particles. For instance, particles can be manufactured from natural materials, synthetic materials, or any combination thereof. Non-limiting examples of materials include ceramics, glass, polymers such as polyethylene, polyvinyl alcohol (PVA), and polystyrene, metals, and any combination thereof.

The size of particles suitable for use in a method of the instant disclosure can and will vary depending on the device, the size of the lumen of the device, the method in which the device is intended for use, and the desired level of resolution of the testing method among other parameters. In some aspects, the device is a medical device. The medical device can be as described in Section I(a) herein above.

Particles used in a method of the instant disclosure can have an accurate validated size distribution and shape. Particle size standards may be used to validate sizing instruments across their dynamic ranges. They are suitable for use in the performance of routine instrument calibration checks and corrections, and in the support of practice standards, such as those published by ISO, ASTM International, CEN, NIST and other organizations. Additionally, the use of reference material permits the standardization of results between runs, instruments, and laboratories, and over time. In some aspects, the particles are NIST (National Institute of Standards and Technology) Traceable Size Standards. NIST traceability provides an official, objective third-party comparison of beads to a known standard and maintained by the National Institute of Standards and Technology.

When the device is a medical device intended for use during a medical procedure, the particle can have a diameter equal to or significantly smaller than the diameter of a particle deemed clinically safe. Particles deemed clinically safe are particles having a diameter significantly smaller than the diameter of an embolic particle. For instance, a particle of the instant disclosure can have a diameter of about 90 microns, about 70 microns, about 50 microns, about 90 microns or less, about 70 microns or less, about 50 microns or less, 150 microns or less, 200 microns or less, about 20 microns to about 150 microns, about 225 microns to about 250 microns, about 75 microns to about 250 microns, about 90 microns to about 600 microns, about 50 microns to about 300 microns, about 40 nm to 1 micron, about 1 nm to about 10 microns, or about 200 nm to about 20 microns. In some aspects, the diameter of particles suitable for use in a method of the instant disclosure have a diameter of about 50 microns or less. In some aspects, the particles are NIST traceable particle size standard polystyrene bead having a diameter of about 50 microns.

B. Immobilizing Particles

Occluding the lumen comprises immobilizing a defined number of particles in the lumen of the device. The test method is described further below in Section I(c).

The method comprises isolating the defined number of particles, introducing the isolated particles into the lumen of the device, immobilizing the particles in the lumen, and optionally confirming the presence of the particles in the lumen. As used herein, the term "immobilize" refers to the sufficient immobilization of the particles in the lumen to maintain the position of the particles in the lumen or to remain in the lumen even when subjected to the forces exerted on the particles during flow rate measurement. Flow rate measurement of the instant disclosure can be described herein further below in Section I(c). It will be understood that the defined number of particles can also be immobilized in a lumen of a device by first introducing particles into the lumen of the device, immobilizing a defined number of the introduced particles, and removing particles that were not immobilized to thereby generate a lumen comprising the defined number of particles immobilized in the lumen of the device.

The defined number of particles to be immobilized in the lumen of a device can and will vary depending on the device and the acceptance criteria to be determined for a device among other variables. For instance, acceptance criteria can be determined for one particle having a first diameter or more than one particle having a combined diameter equal to or approaching the first diameter.

The defined number of particles can be 1, 2, 3, 4, 5, 6, 7, 8, 9, 10, 20, 30, 40, 50, 60, 70, 80, 90, 100, 500, 1000 or more particles, about 1 to about 50 particles, about 10 to about 100 particles, or about 20 to about 200 or more particles can be immobilized in the lumen of a representative device. In some aspects, a lumen of a device is occluded by immobilizing a single particle in a lumen of the device. In some aspects, a lumen of a device is occluded by immobilizing a single particle having a diameter of about 50 microns or less. In some aspects, a lumen of a device can be occluded with more than one particle each having a diameter smaller than about 50 microns, wherein a flow rate measurement obtained for a device occluded with the more than one particle is significantly similar to a flow rate measurement for the device when occluded with a 50 micron particle.

Any method or combination of methods capable of manipulating the defined number of particles can be used in a method of the instant disclosure for isolating and introducing the particles into the lumen of the device. The methods can and will vary depending on the particles, and the method or combination of methods used to isolate, introduce, immobilize, and optionally confirm the presence of the particles in the lumen among other variables. Precise methods for particle confinement and manipulation are known in the art and can be as described in Tanyeri and Schroeder (Nano Lett. 2013 Jun. 12; 13(6): 2357-2364), Zhang et al, (Microfluidics and Nanofluidics volume 24, 2020, Article number: 24), and Tenje et al., (Anal. Chem. 2018, 90, 1434-1443), the disclosures of all of which are incorporated herein in their entirety.

Non-limiting examples of methods capable of precisely manipulating particles include diluted solution comprising a defined number of particles as determined statistically in a suspension comprising the beads, hydrodynamics, use of forces based on optical, electrical, magnetic, and acoustic potential fields, self-driven microbots, artificial cilia, and any combination thereof. The methods can be performed using microfluidic devices, where fluids are manipulated in microchannels. Advantages for using microfluidic devices include (i) high precision and throughput, (ii) flexible spatial and temporal control over fluid flow, (iii) in situ real-time observation, and (iv) the possibility of diverse function integration by exploiting the full capability offered by microengineering.

In some aspects, particles of the instant disclosure are manipulated using hydrodynamic methods. Hydrodynamic methods for particle manipulation utilize sophisticated microchannel networks in microfluidic devices to control particles primarily through balancing opposing transverse forces acting on the particles moving along a microfluidic channel. Examples of hydrodynamic forces are (1) the wall repulsion force (Fwall) originating from the asymmetry of the vorticity around the particles, pushing the particles away from the wall, and (2) the shear-gradient lift force (Fshear) originating from the curvature of the shear flow profile, which leads the particles to migrate away from the central axis. Due to the competition between these two forces, particles suspended in the fluid migrate across streamlines when flowing downstream, and finally equilibrate at a specific location in the channel's cross section. The lateral equilibrium positions of the particles depend on the particle properties (size and deformability), channel size, flow rate and fluid properties (mass density and viscosity).

In some aspects, particles of the instant disclosure are manipulated using acoustic methods. The acoustic method for the manipulation of particles, termed acoustic tweezers, offers a non-contact mode of particle handling. In a typical standing-wave-based acoustic tweezer, the transducer converts electrical signals into acoustic waves. The interference between waves reflected back and forth by the reflection and matching layer form standing waves and establish a pressure distribution in the fluid. The fundamental theory on particle manipulation utilizing acoustic tweezers shows that particles tend to gather at either the pressure nodes or the antinodes of the acoustic wave, under the impact of acoustic radiation forces acting on the particle. The acoustic method can be applied to all types of suspended particles that have acoustic properties that differ from those of the surrounding medium (i.e., the liquid in which the particles are suspended). Acoustic tweezers form a versatile tool for particle manipulation because of their favorable properties including (i) the ability to manipulate particles in a variety of different media (for example, air, aqueous solutions, undiluted blood, and sputum); (ii) the ability to manipulate particles, cells, and organisms across a wide range of length scales, from nanometers (for example, exosomes and nanowires) to millimeters (for example, *C. elegans*); and (iii) the ability to select and to manipulate a single particle or a large group of particles (for example, billions of cells).

In some aspects, particles of the instant disclosure are manipulated using electrical fields. Particles can be manipulated with electrical fields using methods such as electrophoresis, electro-osmosis, and dielectrophoresis. Electrophoresis (EP) is the movement of an electrically charged surface relative to a stationary liquid, induced by an applied electric field. This effect can be used to transport, sort, or trap charged particles within a liquid. Electro-osmosis (EO) is the movement of a liquid relative to a charged (AC electro-osmosis, ACEO) or polarizable (Induced-Charge Electro-osmosis, ICEO) surface (for example of a microchannel) induced by an electric field. In both ACEO and ICEO, an electrical double layer (EDL) is established at the liquid—solid interface. The counter-ions in the liquid phase of the EDL can be set into motion by applying an electric field parallel to the wall. The mobile ions drag bulk liquid in the direction of the electric force. ACEO can generate strong liquid flow when using well-designed electrode patterns on the surface, and this flow can be used to manipulate particles. ICEO in combination with a rotating electrical field can be used to trap cells and particles on an electrode array when the electrodes are well designed. In DEP, a non-charged dielectric particle is subjected to a dielectric force in a non-uniform (often Alternating Current) electric field. The strength of the force depends on the dielectric properties of both the surrounding medium and the particle, on particle shape and size, and on the frequency of the applied electric field. This force moves the particle towards or away from the stronger electric field: (i) when particles have higher permittivity than the surrounding fluid they are pushed towards the stronger electric field, and this is called positive dielectrophoresis (pDEP); (ii) when having lower permittivity than the fluid the particles are repelled from the higher electric field, which is consequently called negative dielectrophoresis (nDEP). Dielectrophoresis is extensively used for particle trapping. Advantages of dielectrophoresis are that it works for non-charged particles as long as they are polarizable, and that it offers flexibility in setting particle sorting thresholds (e.g., particle size) simply by adjusting the electric field frequency.

In some aspects, particles of the instant disclosure are manipulated using magnetic methods. With magnetic methods, use is made of a magnetic field generated either by a permanent magnet or by electromagnets to manipulate particles. In a non-uniform magnetic field, a magnetic or magnetically labelled particle is attracted towards the higher magnetic field. The magnetic force depends on the magnetic field gradient and also on the size and magnetic properties of the particle. The shape of the magnetic particles can be tuned to enhance the controllability of the particle manipulation. For example, helical magnetic microstructures have been developed with controllable transportation direction induced by a rotating magnetic field. Also, collective behavior of magnetic microparticles can be exploited to induce swarm-like behavior with control over transportation and navigation in fluids.

In some aspects, particles of the instant disclosure are manipulated using self-driven microbots. Micro/nanotechnologies can be used to fabricate self-driven micro/nano-robots to transport and release particles/cargos on demand for various applications including isolation of particles. Micro/nano-robots are often bio-inspired, such as hybrid bio-synthetic nanomotors that incorporate motor proteins such as kinesin, myosin, RNA polymerase, F1—adenosine triphosphate synthase, or living organisms such as *Mycoplasma* mobile bacteria and flagellated cells into synthetic systems. Non-limiting examples of self-driven microbots include catalytic reaction-powered microbots such as an Au—Pt bimetallic nanorod, magnetic carbon nanotube (Au/Ni/Au/PtCNT) nanoshuttles, and microtubular jet engines fabricated by rolling-up polymer films.

In some aspects, particles of the instant disclosure are manipulated using artificial cilia. Biological cilia are slender microscopic hair-like protrusions of cells with a typical length between 2 and 15 μm found to exist ubiquitously in nature. This organelle has evolved to possess versatile functionalities including sensing, pumping, particle manipulation such as cell, and food transportation and antifouling. Specific examples are (1) active cilia covering the outer surfaces of mollusks and coral can generate local currents, shielding away sand and preventing settlement of a wide variety of marine fouling organisms; (2) motile cilia line the windpipe and the lungs of the human body, helping to clean up mucus and dust out of the respiratory tract; (3) motile cilia line the inner walls of the fallopian tubes, transporting egg cells to the uterus; (4) cilia grow in the mouth of some marine suspension microorganisms, facilitating feeding. All these favorable functionalities are dominated by the substantial local flow generated by the asymmetric motion of cilia in combination with the direct contacting forces applied on the particles by cilia beating. A non-limiting example of artificial cilia include magnetic artificial cilia (MAC) made of a polydimethylsiloxane (PDMS)—superparamagnetic particle (carbonyl iron powder, CIP) composite material.

Methods suitable for immobilizing a defined number of particles in the lumen can and will vary depending on the particles, and the method or combination of methods used to isolate, introduce, and optionally confirm the presence of the particles in the lumen among other variables. Non-limiting examples of methods that can be used to immobilize particles in the lumen of a device include hydrodynamics, use of forces based on optical, electrical, magnetic, and acoustic potential fields, self-driven microbots, artificial cilia, and any combination thereof.

Methods of confirming the presence of the particles in the lumen can and will vary depending on the particles, and the method or combination of methods used to isolate, and introduce, the particles into the lumen among other variables. Non-limiting examples of methods that can be used to confirming the presence of the particles include visual inspection such as inspection using a microscope, magnetic detection of magnetic particles such as using magnetometers, radioactivity of radioactive particles, fluorescence of fluorescent particles, flow cytometry, enzyme-linked immunoassays, functional assays, and any combination thereof. The methods of detection can also be used to detect particles in solution during manipulation in other steps in the method A single method or a combination of methods for manipulating particles, wherein the methods can be the same or different for each step of immobilizing the particles. The choice of methods can and will vary depending on the particles, the device, the method used to measure flow rate, the methods used to isolate, introduce, immobilize, and confirm the presence of a defined number of particles in the lumen of the device, among other variables. For instance, if a particle is isolated by trapping in light tweezers, the light tweezers can also be used to introduce the particle into the lumen of the device and immobilizing the particle in the lumen of the device. Alternatively, a particle can be isolated and introduced into the lumen by trapping in light tweezers, and the particle can be immobilized in the lumen of the device using an adhesive.

In some aspects, particles of the instant disclosure are manipulated in diluted solution comprising a defined number of particles as determined statistically. In such aspects, the number of particles can be isolated by diluting a solution comprising the one or more particle, and aliquoting a volume of the solution statistically calculated to comprise the desired number of particles. The number of particles can further be confirmed in each aliquot, for instance, visually under magnification. Sensitivity and detectability of particles using visual inspection can further be facilitated or enhanced using colored particles or fluorescent particles that emit bright colors when illuminated by UV light. In some aspects, the bead solution comprises a surfactant. Surfactants can be as described in Section I(b)(C).

In some aspects, the particles are immobilized using an adhesive. In some aspects, the bead solution comprises and adhesive. In some aspects, the bead solution comprises a surfactant and an adhesive. Adhesives can be as described in Section I(b)(D).

In some aspects, the particles are immobilized in a lumen of the device by introducing a bead solution comprising a defined number of particles isolated using visual inspection and an adhesive, and adhering the particles in the lumen. Generally, particles are suspended in a solution comprising an adhesive for attaching particles in the lumen and introduced into the lumen of the representative device. The particles can be allowed to flow toward the middle of the lumen. The solution can then be removed and dried of any residual moisture to remove all fluid to not hinder data collection. The solution can be removed by allowing the solution to evaporate. In some aspects, the solution is oven incubated to remove residual moisture that could confound the data. An oven can be a recirculating air oven. In some aspects, the lumen is dried by incubating the device in a recirculating air oven for about 48 hours at about 65° C.

C. Surfactants

Surfactants can be included in a bead solution to facilitate introduction into a lumen and prevent agglomeration of the particles. The solution can comprise one surfactant or a system of surfactants comprising one or more surfactants.

The bead solution can comprise about 00.01%, 0.05%, 0.1%, 0.5%, 1%, 1.5%, 2%, 2.5%, 3%, 3.5%, 4%, 4.5%, 5%, 6%, 7%, 8%, 9%, or less than about 10% surfactant. The bead solution can comprise less than about 0.05%, 0.1%, 0.5%, 1%, 1.5%, 2%, 2.5%, or less than about 3% surfactant. In some aspects, the bead solution comprises less than about 00.01%, 0.05%, 0.1%, 0.5%, 1%, 1.5%, 2%, 2.5%, 3%, 3.5%, 4%, 4.5%, 5%, 6%, 7%, 8%, 9%, or less than about 10% surfactant. The bead solution can comprise less than about 00.05%, 0.1%, 0.5%, 1%, 1.5%, 2%, 2.5%, or less than about 3% surfactant. In some aspects, the bead solution comprises less than about 0.05%, 0.1%, 0.5%, 1%, 1.5%, 2%, 2.5%, or less than about 3% surfactant. In some aspects, the bead solution comprises less than about 0.3%, 0.2%, or less than about 0.1% surfactant.

A variety of surfactants may be included in the surfactant system. Non-limiting examples of suitable nonionic surfactants include sorbitan esters such as sorbitan (Span 20), sorbitan monopalmitate (Span 40), sorbitan monostearate (Span 60), sorbitan monooleate (Span 80), sorbitan sesquioleate (Span 83), sorbitan trioleate (Span 85), sorbitan isostearate (Span 120), or combinations thereof; polyethoxylated sorbitan esters such as polyoxyethylene (20) sorbitan monolaurate (Tween 20), polyoxyethylene (4) sorbitan monolaurate (Tween 21), polyoxyethylene (20) sorbitan monopalmitate (Tween 40), polyoxyethylene (20) sorbitan monostearate (Tween 60), polyoxyethylene (4) sorbitan monostearate (Tween 61), polyoxyethylene (20) sorbitan tristearate (Tween 65), polyoxyethylene (20) sorbitan monooleate (Tween 80), or combinations thereof; polyglycerol esters of fatty acids such as triglycerol monolaurate, triglycerol monooleate, triglycerol monostearate, polyglycerol oleate, polyglycerol, laurate, polyglycerol stearate, polyglycerol polyricinoleate, and so forth; and other nonionic surfactants such as glyceryl monolaurate, glyceryl monooleate, glyceryl monostearate, glycol distearate, glycol stearate, ceteareth-20, cetearyl glycoside, ceteth-2, ceteth-10, ceteth-20, cocamide MEA, isoceteth-20, isosteareth-20, laureth-4, laureth-23, methyl glucose sesquistearate, oleth-2, oleth-10, oleth-20, PEG-100 stearate, PEG-20 almond glycerides, PEG-60 almond glycerides, PEG-20 methyl glucose sesquistearate, PEG-7 hydrogenated castor oil, PEG-25 hydrogenated castor oil, PEG-35 hydrogenated castor oil, PEG-40 hydrogenated castor oil, PEG-60 hydrogenated castor oil, PEG-200 hydrogenated glyceryl palmate, PEG-30 dipolyhydroxystearate, PEG-4 dilaurate, PEG-40 sorbitan peroleate, PEG-7 olivate, PEG-7 glyceryl cocoate, PEG-8 dioleate, PEG-8 laurate, PEG-8 oleate, PEG-80 sorbitan laurate, PEG-40 stearate, propylene glycol isostearate, stearamide MEA, steareth-2, steareth-20, steareth-21, steareth-100, polyoxyethylene (7-8) p-t-octyl phenol (Triton X-114), polyoxyethylene (9-10) p-t-octyl phenol (Triton X-100), polyoxyethylene (9-10) nonylphenol (Triton N-101), polyoxyethylene (9) p-t-octyl phenol (Nonidet P-40), polyoxyethylene (10) cetyl ether (Brij 56), polyoxyethylene (20) cetyl ether (Brij 58), polyoxyethyleneglycol dodecyl ether (Brij 35), copolymers of ethylene oxide and propylene oxide (e.g., Pluronic F-68, Pluronic F-127, etc.), dimethyldecylphosphine oxide (APO-10), dimethyldodecylphosphine oxide (APO-12), cyclohexyl-n-ethyl-β-D-maltoside, cyclohexyl-n-hexyl-β-D-maltoside, cyclohexyl-n-methyl-β-maltoside, n-decanoylsucrose, n-decyl-β-D-glucopyranoside, n-decyl-β-maltopyranoside, n-decyl-β-D-thiomaltoside, n-dodecanoyl sucrose, decaethylene glycol monododecyl ether, N-decanoyl-N-methylglucamine, n-decyl α-D-glucopyranoside, decyl β-D-maltopyranoside, n-dodecanoyl-N-methylglucamide, n-dodecyl α-D-maltoside, n-dodecyl β-D-maltoside, heptane-1,2,3-triol, heptaethylene glycol monodecyl ether, heptaethylene glycol monododecyl ether, heptaethylene glycol monotetradecyl ether, n-hexadecyl β-D-maltoside, hexaethylene glycol monododecyl ether, hexaethylene glycol monohexadecyl ether, hexaethylene glycol monooctadecyl ether, hexaethylene glycol monotetradecyl ether, methyl-6-O—(N-heptylcarbamoyl)-α-D-glucopyranoside, nonaethylene glycol monododecyl ether, N-nonanoyl-N-methylglucamine, N-nonanoyl-N-methylglucamine, octaethylene glycol monodecyl ether, octaethylene glycol monododecyl ether, octaethylene glycol monohexadecyl ether, octaethylene glycol monooctadecyl ether, octaethylene glycol monotetradecyl ether, octyl-β-glucoside, octyl-β-thioglucoside, octyl-β-D-glucopyranoside, octyl-β-D-1-thioglucopyranoside, pentaethylene glycol monodecyl ether, pentaethylene glycol monododecyl ether, pentaethylene glycol monohexadecyl ether, pentaethylene glycol monohexyl ether, pentaethylene glycol monooctadecyl ether, pentaethylene glycol monooctyl ether, polyethylene glycol diglycidyl ether, polyethylene glycol ether, polyoxyethylene (10) tridecyl ether, polyoxyethylene (100) stearate, polyoxyethylene (20) isohexadecyl ether, polyoxyethylene (20) oleyl ether, polyoxyethylene (40) stearate, polyoxyethylene (50) stearate, polyoxyethylene (8) stearate, polyoxyethylene bis(imidazolyl carbonyl), polyoxyethylene (25) propylene glycol stearate, saponin from Quillaja bark, tetradecyl-β-D-maltoside, tetraethylene glycol monodecyl ether, tetraethylene glycol monododecyl ether, tetraethylene glycol monotetradecyl ether, triethylene glycol monodecyl ether, triethylene glycol monododecyl ether, triethylene glycol monohexadecyl ether, triethylene glycol monooctyl ether, triethylene glycol monotetradecyl ether, tyloxapol, n-undecyl β-D-glucopyranoside, octylphenoxypolyethoxyethanol (IGEPAL CA-630), polyoxyethylene (5) nonylphenylether (IGEPAL CO-520), polyoxyethylene (150) dinonylphenyl ether (IGEPAL DM-970), or combinations thereof.

Examples of suitable zwitterionic surfactants include, without limit, lecithins (e.g., a lecithin extracted from soybeans, eggs, milk, marine sources, rapeseed, cottonseed, sunflower, and the like), hydrolyzed lecithins, hydrogenated lecithins, acetylated lecithins, 3-[(3-cholamidopropyl)dimethylammonio]-2-hydroxy propanesulfonate (CHAPSO), 3-[(3-cholamidopropyl)dimethylammonio]-1-propanesulfonate (CHAPS), 3-(4-heptyl)phenyl-3-hydroxypropyl) dimethylammoniopropanesulfonate (C7BzO), 3-(N,N-dimethyloctylammonio) propanesulfonate inner salt (SB3-8), 3-(decyldimethylammonio) propanesulfonate inner salt (SB3-10), 3-(dodecyldimethylammonio) propanesulfonate inner salt (SB3-12), 3-(N,N-dimethyltetradecylammonio) propanesulfonate (SB3-14), 3-(N,N-dimethylpalmitylammonio) propanesulfonate (SB3-16), 3-(N,N-dimethyloctadecylammonio) propanesulfonate (SB3-18), 3-[N,N-dimethyl(3-myristoylaminopropyl)ammonio] propanesulfonate (ASB-14), caprylyl sulfobetaine, capric amidopropyl betaine, capryloamidopropyl betaine, cetyl betaine, cocamidopropyl betaine, C12-14 alkyl dimethyl betaine, cocamidopropyl dimethylaminohydroxypropyl hydrolyzed collagen, N-[3-cocamido)-propyl]-N,N-dimethyl betaine, cocamidopropyl hydroxysultaine, cocamidopropyl sulfobetaine, cocaminobutyric acid, cocaminopropionic acid, cocoamphodipropionic acid, coco-betaine, cocodimethylammonium-3-sulfopropylbetaine, cocoiminodiglycinate, cocoiminodipropionate, coco/oleamidopropyl betaine, cocoyl sarcosinamide DEA, DEA-cocoamphodipropionate, dihydroxyethyl tallow glycinate, dimethicone propyl PG-betaine, N,N-dimethyl-N-lauric acid-amidopropyl-N-(3-sulfopropyl)-ammonium betaine, N,N-dimethyl-N-myristyl-N-(3-sulfopropyl)-ammonium betaine, N,N-dimethyl-N-palmityl-N-(3-sulfopropyl)-ammonium betaine, N,N-dimethyl-N-stearamidopropyl-N-(3-sulfopropyl)-ammonium betaine, N,N-dimethyl-N-stearyl-N-(3-sulfopropyl)-ammonium betaine, N,N-dimethyl-N-tallow-N-(3-sulfopropyl)-ammonium betaine, disodium caproamphodiacetate, disodium caproamphodipropionate, disodium capryloamphodiacetate, disodium capryloamphodipropionate, disodium cocoamphodiacetate, disodium cocoamphodipropionate, disodium isostearoamphodipropionate, disodium laureth-5 carboxyamphodiacetate, disodium lauriminodipropionate, disodium lauroamphodiacetate, disodium lauroamphodipropionate, disodium octyl b-iminodipropionate, disodium oleoamphodiacetate, disodium oleoamphodipropionate, disodium PPG-2-isodeceth-7 carboxyamphodiacetate, disodium stearoamphodiacetate, N,N-distearyl-N-methyl-N-(3-sulfopropyl)-ammonium betaine, ethylhexyl dipropionate, ethyl hydroxymethyl oleyl oxazoline, ethyl PEG-15 cocamine sulfate, isostearamidopropyl betaine, lauramidopropyl betaine, lauramidopropyl dimethyl betaine, lauraminopropionic acid, lauroamphodipropionic acid, lauroyl lysine, lauryl betaine, lauryl hydroxysultaine, lauryl sultaine; linoleamidopropyl betaine, lysolecithin, myristamidopropyl betaine, octyl dipropionate, octyliminodipropionate, oleamidopropyl betaine, oleyl betaine, 4,4(5H)-oxazoledimethanol, palmitamidopropyl betaine, palmitamine oxide, ricinoleamidopropyl betaine, ricinoleamidopropyl betaine/IPDI copolymer, sesamidopropyl betaine, sodium C12-15 alkoxypropyl iminodipropionate, sodium caproamphoacetate, sodium capryloamphoacetate, sodium capryloamphohydroxypropyl sulfonate, sodium capryloamphopropionate, sodium cocaminopropionate, sodium cocoamphoacetate, sodium cocoamphohydroxypropyl sulfonate, sodium cocoamphopropionate, sodium dicarboxyethyl cocophosphoethyl imidazoline, sodium isostearoamphopropionate, sodium lauriminodipropionate, sodium lauroamphoacetate, sodium oleoamphohydroxypropylsulfonate, sodium oleoamphopropionate, sodium stearoamphoacetate, sodium tallamphopropionate, soyamidopropyl betaine, stearyl betaine, trisodium lauroampho PG-acetate phosphate chloride, undecylenamidopropyl betaine, or combinations thereof.

In some aspects, the surfactant is Triton™ X-100, Tween® 20, or combinations thereof.

D. Adhesive

The particles can be immobilized in a lumen of a device by adhering in the lumen using an adhesive. In some aspects, a suitable adhesive is a polymeric adhesive. Non-limiting examples of suitable polymeric glues include epoxy resins, epoxy putty, ethylene-vinyl acetate (a hot-melt glue), phenol formaldehyde resin, polyamide, polyester resins, polyethylene (a hot-melt glue), polypropylene, polysulfides, polyurethane, polyvinyl acetate (PVA), polyvinyl alcohol, polyvinyl chloride (PVC), polyvinyl chloride emulsion (PVCE), polyvinylpyrrolidone (PVP), rubber cement, silicones, silyl modified polymers, and styrene acrylic copolymer. A combination of more than one glue can also be used in a bead solution. In some aspects, the adhesive is a water-based adhesive such as PVP. It will be recognized that the concentration of the glue in a bead solution can and will vary depending on the glue, the particle material, and material of the lumen. However, any concentration of glue sufficient to adhere and maintain the particles in the lumen can be used and can be determined experimentally. In some aspects, the adhesive is PVP.

In some aspects, the bead solution can comprise about 0.001%, 0.005%, 0.01%, 0.05%, 0.1%, 0.5%, 1%, 1.5%, 2%, 2.5%, 3%, 3.5%, 4%, 4.5%, or about 5% adhesive. The bead solution can comprise less than about 0.001%, 0.0055%, 0.01%, 0.05%, 0.1%, 0.5%, 1%, 1.5%, or less than about 2% adhesive. In some aspects, the bead solution comprises less than about 0.01%, 0.05%, 0.1%, 0.5%, or less than about 1% adhesive. In some aspects, the bead solution comprises less than about 0.1%, 0.2%, or less than about 0.3% adhesive. In some aspects, the polymeric adhesive is a polymeric adhesive. In some aspects, the adhesive is a polymeric adhesive, and the solution comprises less than about 0.1%, 0.2%, or less than about 0.3% polymeric adhesive. In one aspect, the polymeric adhesive is an aqueous polymeric adhesive. In some aspects, the adhesive is an aqueous polymeric adhesive, and the solution comprises less than about 0.3%, 0.2%, or less than about 0.1% aqueous polymeric adhesive.

(c) Flow Rate

The method comprises calculating or having calculated a flow rate of a fluid in the lumen of an occluded representative device. A device comprising a lumen can be as described in Section I(a) and a method of occluding a lumen of a device can be as described in Section I(b).

The fluid can be a non-compressible fluid (liquid) or a compressible fluid (gas). Both gas and liquid flow rates can be measured in physical quantities of volumetric or mass flow rates, with units such as liters per second or kilograms per second, respectively. These measurements are related by the material's density. The density of a liquid is almost independent of conditions. This is not the case for gases, the densities of which depend greatly upon pressure, temperature and to a lesser extent, composition. The volumetric flow rate can be given the symbol Q, and the mass flow rate, the symbol $\dot{m}$. For a fluid having density ρ, mass and volumetric flow rates can be related by the following equation $$\dot{m}=\rho Q.$$

In some aspects, the mass flow rate is obtained. Mass flow rate is the mass of a substance which passes per unit of time. Mass flow rates can be defined by the limit, i.e., the flow of mass m through a surface per unit time t:

$$\dot{m} = \lim_{\Delta t \to 0} \frac{\Delta m}{\Delta t} = \frac{dm}{dt}$$

Mass flow rate can also be defined by:

$$\dot{m}=\rho\cdot\dot{V}=\rho\cdot v\cdot A=j_m\cdot A$$

where:

$\dot{V}$ or r Q=volumetric flow rate

ρ=mass density of the fluid v=flow velocity of the mass elements,

A=cross-sectional vector area/surface $J_m$=mass flux

In some aspects, the volumetric flow rate is obtained. Volumetric flow rate (also known as volume flow rate, or volume velocity) is the volume of fluid which passes per unit time. Volumetric flow rates can be defined by the limit, i.e., the flow of volume V through a surface per unit time t $$Q = \dot{V} = \lim_{\Delta t \to 0} \frac{\Delta V}{\Delta t} = \frac{dV}{dt}$$

Volumetric flow rate can also be defined by the equation below, where v is flow velocity and A is the cross-sectional vector area/surface:

$$Q=v\cdot A$$

In some aspects, the fluid is a non-compressible fluid. When the fluid is a non-compressible fluid, the units of measurement can be gallons (U.S. or imperial) per minute, liters per second, bushels per minute, cumecs (cubic meters per second) or acre-feet per day. In oceanography a common unit to measure volume transport (volume of water transported by a current for example) is a sverdrup (Sv) equivalent to $10^6$ $m^3/s$.

In some aspects, the fluid is a compressible fluid (gas). Compressible fluids change volume when placed under pressure, are heated, or are cooled. A volume of gas under one set of pressure and temperature conditions is not equivalent to the same gas under different conditions. References will be made to "actual" flow rate through a meter and "standard" or "base" flow rate through a meter with units such as acm/h (actual cubic meters per hour), $sm^3$/sec (standard cubic meters per second), kscm/h (thousand standard cubic meters per hour), LFM (linear feet per minute), or MMSCFD (million standard cubic feet per day). In some aspects, the unit of measurement is standard cubic centimeters per minute (sccm). Gas mass flow rate can be directly measured, independent of pressure and temperature effects, with thermal mass flowmeters, Coriolis mass flowmeters, or mass flow controllers.

Flow rate in a tube is affected by the physical characteristics of the tube comprising the lumen such as tube length, tube inner diameter and shape, curves or device-specific parts attached along the fluid flow of the lumen, and viscosity of the fluid among other variables. Flow rate can be governed by the Navier-Stokes equations which are certain partial differential equations which describe the motion of viscous fluid substances. The Navier-Stokes equations describe the physics of many phenomena of scientific and engineering interest. They may be used to model the weather, ocean currents, water flow in a pipe and air flow around a wing. Navier-Stokes equations can be used to derive equations that govern flow of a fluid in a tube such as a lumen such as the Hagen-Poiseuille equation, the Darcy—Weisbach equation, and the Hazen—Williams equation.

In some aspects, the flow rate is determined using the Hagen-Poiseuille equation:

$$\Delta Q = \frac{\pi \Delta P d^4}{128 \mu l}$$

Where ΔP is the pressure drop of a liquid having viscosity μ in a pipe having a length l and a diameter d.

Obtaining a flow rate measurement comprises measuring the flow rate of a fluid in the lumen by measuring the volume or mass of the fluid through the lumen at a certain pressure or measuring the pressure of the fluid at which a certain flow of fluid is through the lumen. Accordingly measuring flow rate of a fluid comprises measuring the pressure of the fluid, the mass or volume flow of the fluid, or both.

The flow of fluid can be determined using a flow meter. Non-limiting examples of flow meters include mechanical flowmeters; pressure-based meters; variable-area flowmeters; optical flowmeters; open-channel flow measurement; thermal mass flowmeters such as the MAF sensor; vortex flowmeters; sonar flow measurement; electromagnetic, ultrasonic, and Coriolis flowmeters; and laser Doppler flow measurement.

In some aspects, the flow meter of the instant disclosure is a mechanical flow meter. Non-limiting examples of mechanical flow meters include piston meter or rotary piston, such as an oval gear meter, a gear meter such as helical gear and nutating disk meter, turbine flowmeter, Woltman meter, single jet meter, paddle wheel meter, multiple jet meter, pelton wheel, and current meter.

In some aspects, the flow meter of the instant disclosure is a pressure-based meter. Non-limiting examples of pressure based meters include, venturi meter, orifice plate, DalI tube, Pitot tube, averaging pitot tube, cone meters, and linear resistance meters.

In some aspects, the flow meter of the instant disclosure is an open channel flow meter. Non-limiting examples of open channel flow meters include level to flow, area/velocity, dye testing, and acoustic Doppler velocimetry.

In some aspects, the flow meter is an electromagnetic, ultrasonic and Coriolis flowmeter. Non-limiting examples of electromagnetic, ultrasonic and Coriolis flowmeters include magnetic flowmeters, non-contact electromagnetic flowmeters, ltrasonic flowmeters (Doppler, transit time), and coriolis flowmeters.

The pressure of the fluid can be determined using a pressure sensor. Pressure sensors are instruments or devices that translate the magnitude of the physical pressure exerted on the sensor into an output signal that can be used to establish a quantitative value for the pressure. There are many different types of pressure sensors known in the art, which function similarly but rely on different underlying technologies to make the translation between pressure and an output signal. Non-limiting examples of pressure sensor technologies include:

- Potentiometric pressure sensors. Potentiometric pressure sensors use a Bourdon tube, capsule, or bellows which drives a wiper arm, providing relatively course pressure measurements.
- Inductive pressure sensors. Inductive pressure sensors use a linear variable differential transformer (LVDT) to vary the degree of inductive coupling that occurs between the primary and secondary coils of the transformer.
- Capacitive pressure sensors. Capacitive pressure sensors use a diaphragm that is deflected by the applied pressure, which results in a change in the capacitance value, which can then be calibrated to provide a pressure reading.
- Piezoelectric pressure sensors. Piezoelectric pressure sensors rely on the ability of materials such as ceramic or metalized quartz to generate an electrical potential when the material is subjected to mechanical stress.
- Strain gauge pressure sensors. Strain gauge pressure sensors rely on a measurement of the change in resistance that occurs in a material such as silicon when it is subjected to mechanical stress, known as the piezoresistive effect.
- Variable reluctance pressure sensors. Variable reluctance pressure sensors make use of a diaphragm that is contained in a magnetic circuit. When pressure is applied to the sensor, the diaphragm deflection causes a change in the reluctance of the circuit and that change can be measured and used as an indicator of the applied pressure.

(d) Calculating a Test Limit Value

A method of determining acceptance criteria comprises using a probability model to calculate the acceptance criteria for the representative device. More specifically, a method of determining acceptance criteria comprises using a probability model to calculate a flow rate for a device representative of a device of interest (a representative device) occluded with a defined number of one or more occluding particles wherein the calculated flow rate is the acceptance criteria for the device to be inspected. An inspected device is calculated to be occluded if a flow rate measurement for the inspected device is equal to or significantly lower than the acceptance criteria, and the inspected device is determined to be unoccluded if the flow measurement in the inspected device is higher than the acceptance criteria. Particles can be as described in Section I(b)(A) herein above, occluding the device can be as described in Section I(b), and flow rate measurements can be obtained for occluded or unoccluded devices as described herein above in Section I(c). In some aspects, the flow rate measurements for an occluded device are obtained for a representative device occluded with a single 50 micron particle.

In some aspects, the acceptance criteria for a device of interest is an upper test limit (UTL) flow rate calculated using a probability model. Accordingly, an inspected device is determined to be occluded if a calculated flow rate for the inspected device is equal to or lower than a UTL flow rate calculated for the device of interest, and the inspected device is determined to be unoccluded if the flow rate measurement in the inspected device is higher than the UTL flow rate.

In some aspects, the UTL flow rate is calculated by generating a probability plot at a confidence interval using flow rate measurements for a representative device occluded with a defined number of one or more occluding particles, fitting a distribution line for a statistical distribution function to the flow rate measurements, and determining a UTL flow rate value at a confidence level on the fitted distribution line. In some aspects, the method further comprises incorporating a system error into the UTL flow rate value to calculate a corrected UTL flow rate value at a confidence level. The error margin can be as provided by the manufacturer of the mass flow detection device. In some aspects, the method further comprises applying the corrected UTL flow rate to the statistical distribution function of the measured flow rates to calculate a corrected confidence level.

A probability plot can be generated at a confidence interval of about 70% or higher, 80% or higher, 90% or higher, at a confidence level ranging from about 80% to about 100%, from about 80% to about 100%, from about 90% to about 100%. In some aspects, the probability plot is generated at a confidence interval of about 85% or higher, 90% or higher, 95% or higher, or 99% or higher. In some aspects, the probability plot is generated at a confidence interval of about 85%, 86%, 87%, 88%, 89%, 90%, 91%, 92%, 93%, 94%, 95%, 96%, 97%, 98%, 99,%, or about 100%. In some aspects, the probability plot is generated at a confidence interval of about 95%.

The UTL flow rate value can be determined on the fitted line at a confidence interval of about 70% or higher, 80% or higher, 90% or higher, at a confidence level ranging from about 80% to about 100%, from about 80% to about 100%, from about 90% to about 100%. In some aspects, the UTL flow rate is determined at a confidence interval of about 85% or higher, 90% or higher, 95% or higher, or 99% or higher. In some aspects, the UTL flow rate is determined at a confidence interval of about 85%, 86%, 87%, 88%, 89%, 90%, 91%, 92%, 93%, 94%, 95%, 96%, 97%, 98%, 99,%, or about 100%. In some aspects, the UTL flow rate is determined at a confidence interval of about 90% or higher, about 91% or higher, about 92% or higher, about 93% or higher, about 94% or higher, about 95% or higher, about 96% or higher, about 97% or higher, about 98% or higher, or about 99% or higher. In some aspects, the UTL flow rate is determined at a confidence interval of about 90%. In some aspects, the UTL flow rate is determined at a confidence interval of about 95%. In some aspects, the UTL flow rate is determined at a confidence interval of about 98%. In some aspects, the UTL flow rate is determined at a confidence interval of about 99% or higher. In some aspects, the UTL flow rate is determined at a confidence interval higher than about 99%.

Accordingly, a UTL flow rate can be the UTL flow rate at a 70/70 confidence interval or higher. In some aspects, the UTL flow rate is the UTL flow rate at a 95/85 confidence interval or higher. For instance, upper test limit flow rate can be the upper boundary of a probability plot at a confidence interval of 95/85, 95/86, 95/87, 95/88, 95/89, 95/90, 95/91, 95/92, 95/93, 95/94, 95/95, 95/96, 95/97, 95/98, 95/99 or above. In some aspects, the upper test limit about 95/99.01, 95/99.05, 95/99.1, 95/99.15, 95/99.20, 95/99.25, 95/99.30, 95/99.35, 95/99.40, 95/99.45, 95/99.50, 95/99.55, 95/99.60, 95/99.65, 95/99.70, 95/99.75, 95/99.80, 95/99.85, 95/99.90, 95/99.95, or about 95/99 or above. In some aspects, the upper test limit about 95/99.81, 95/99.82, 95/99.83, 95/99.84, 95/99.85, 95/99.86, 95/99.87, 95/99.88, 95/99.89, 95/99.90, 95/99.91, 95/99.92, 95/99.93, 95/99.94, 95/99.95, 95/99.96, 95/99.97, 95/99.98, 95/99.99 or above.

Non-limiting examples of statistical distribution functions suitable for fitting a distribution line can be exponential distribution, gamma distribution, logistic distribution. loglogistic distribution, lognormal distribution, normal distribution, extreme value distributions, Weibull distribution, and any combination thereof.

Figure 27:
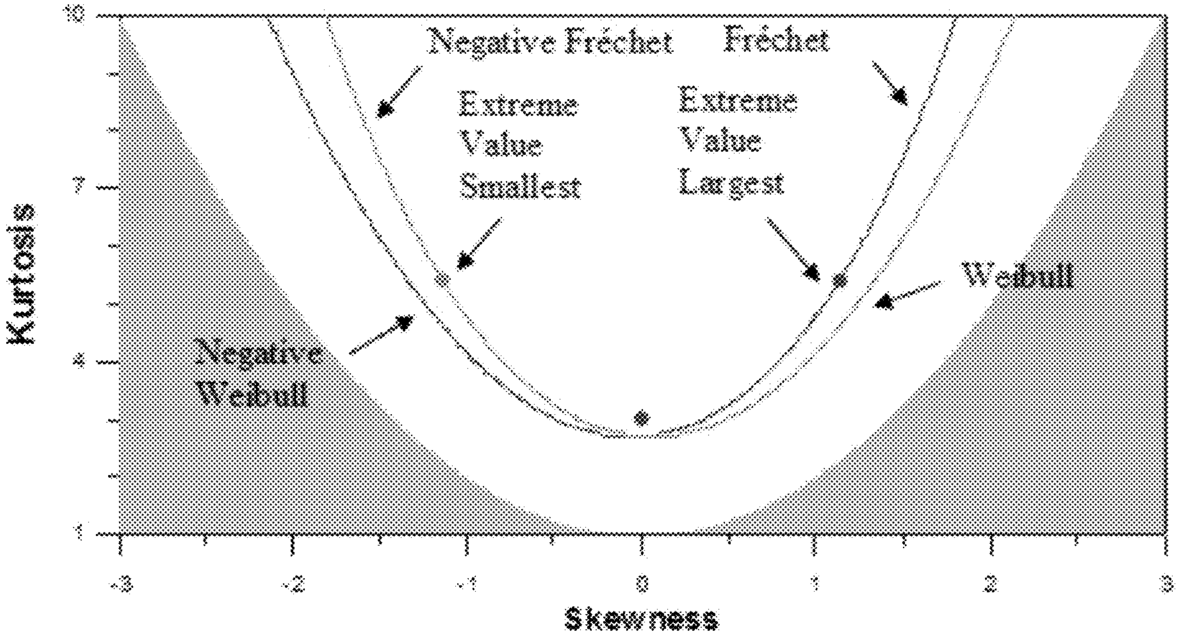
FIG. 27. Skewness-kurtosis plot representing the three smallest extreme value family of distributions.

In some aspects, the statistical distribution function for fitting a distribution line is an extreme value statistical distribution. Extreme value distributions are used extensively to model the distribution of streamflow, flooding, rainfall, temperature, wind speed, and other meteorological variables, as well as material strength and life data. The extreme value family of distributions is made up of three distributions: Weibull, negative Fréchet and smallest extreme value. It covers any specified average, standard deviation, and any skewness above −5.6051382. Together they form a 3-parameter family of distributions that is represented by a curve on a skewness-kurtosis plot as shown in FIG. 27. The Weibull distribution covers the portion of the curve with skewness above −1.139547. The negative Fréchet distribution covers the portion of the curve with skewness below −1.139547. The smallest extreme value distribution handles the remaining case of skewness equal to −1.139547.

In some aspects, the statistical distribution function for fitting a distribution line is the smallest extreme value distribution. The smallest extreme value distribution is the limiting distribution (as n approaches infinity) of the smallest value among n independent random variables each having the same continuous distribution.

In some aspects, the UTL flow rate is calculated using the following steps;

1) measuring or having measured flow rates in more than one of a device of interest occluded with a single 50 micron particle;
2) generating a probability plot at 95% confidence interval using the flow rates of step (1);
3) calculating a fitted distribution line for a smallest extreme value distribution of the plot of step (2);
4) calculate the UTL flow rate at 90% confidence level using the fitted distribution line of step (3); and optionally
5) incorporating a system error of 0.5% of full range into the UTL flow rate of step (4) to determine a corrected UTL flow rate value at 90% confidence level;

wherein the flow rate of step (4) or step (5) is the upper test limit at 95/90 confidence interval (the 95/90 UTL flow rate), and wherein an inspected device is determined to be occluded if a flow rate measurement for the inspected device is equal to or lower than the 95/90 UTL flow rate, and the inspected device is determined to be unoccluded if the flow measurement in the inspected device is higher than the 95/90 UTL flow rate.

In some aspects, the method further comprises applying the corrected 95/90 UTL flow rate of step 5 to the smallest extreme value distribution function of the measured flow rates to determine a corrected confidence interval of the corrected UTL flow rate.

(e) Aspects of a Method of Determining Acceptance Criteria

In some aspects, the fluid is a compressible fluid. In some aspects, the fluid is a gas. In some aspects, a method of measuring fluid flow rate comprises delivering the gas through the lumen at a rate required to maintain a predetermined pressure. The predetermined pressure can be any pressure at which a single occluding particle can significantly reduce the flow rate through the lumen. Impacted by the cross-sectional area of the blockage, a fully occluded device will allow little to no quantity ($\Delta AQ=0$) of gas to exit the lumen, thereby requiring little to no additional flow of air to maintain the charge pressure. Non-occluded devices will allow full and rapid flow of gas exiting the lumen, as there is no impedance other than that provided by the properties of the lumen itself (i.e., material, geometry, surface finish, etc.). This will require a much higher flow of air to maintain the charge pressure. Partially occluded devices will impede this flow to the degree by which they are obstructed as defined in the Hagen-Poiseuille equation above, requiring a flow of air between that of the fully and non-occluded devices.

In some aspects, a method of obtaining a flow rate measurement comprises installing the device in a flow measuring instrument and charging the lumen of the device to a predetermined pressure with a fluid. Fluid can be delivered through the lumen at a sufficient rate to maintain the predetermined pressure, thereby obtaining the flow rate. In some aspects, the fluid is gas, and the flow rate is calculated using the Hagen-Poiseuille equation, and is expressed in standard cubic centimeters per minute (sccm). One sccm indicates the flow rate of one cubic centimeter per minute of a fluid.

Figure 28:
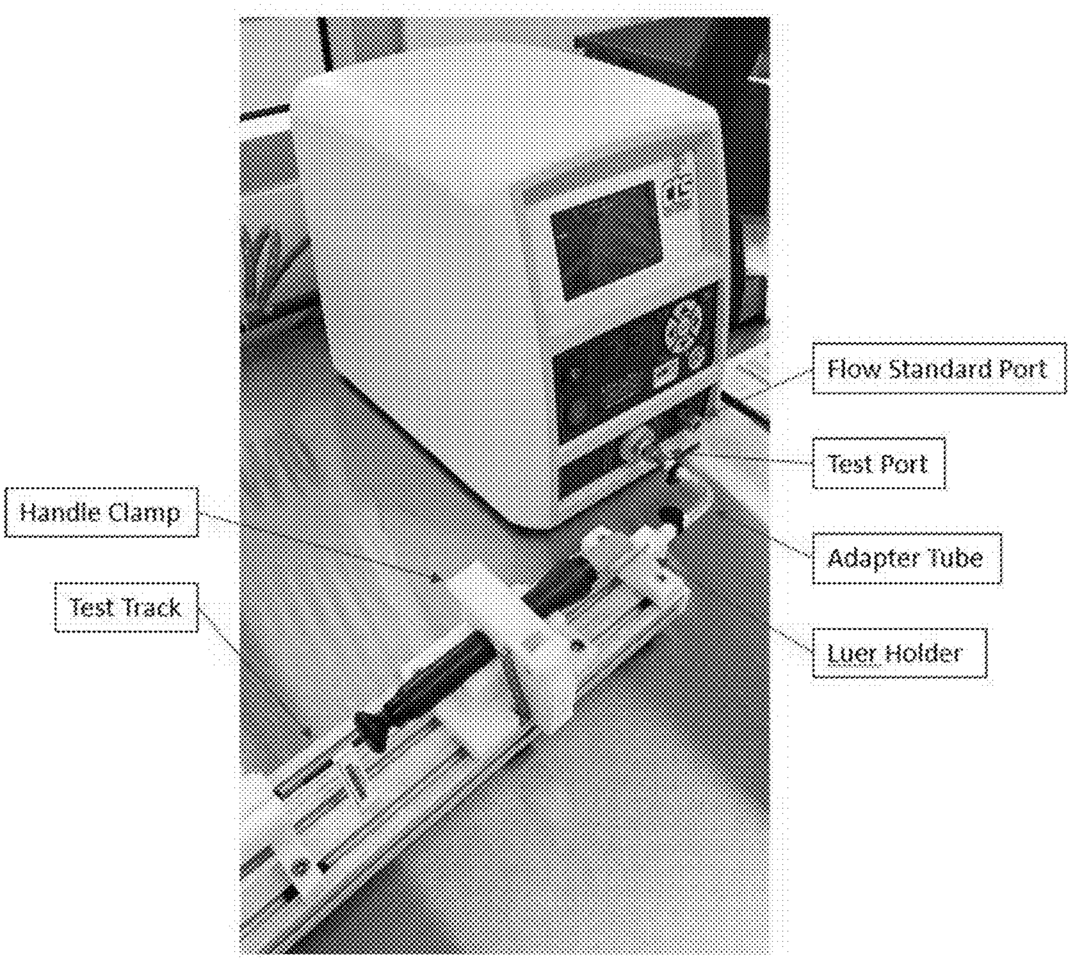
FIG. 28. Sentinel Blackbelt Test System from Cincinnati Test Systems (CTS) component identification and setup/positioning.

Any flow rate measurement instrument comprising a suitable flow meter can be used in this method, provided the device can accommodate a device of interest, and provide the desired pressure. For instance, the flow rate measuring device is able to accommodate a device comprising a lumen having the correct lumen size, and capable of providing an unimpeded flow rate of any subject device sufficient for the development of an inspection method. When the device is a medical device comprising a microlumen, the flow rate measurement instrument can be the Sentinel Blackbelt Test System from Cincinnati Test Systems (CTS; FIG. 28).

As explained herein above in Section I(c), flow rate in a tube is affected by the physical characteristics of the tube comprising the lumen such as tube length, tube inner diameter and shape, curves or device-specific parts attached along the fluid flow of the lumen, and viscosity of the fluid among other variables. Accordingly, flow characteristics can differ between different types of devices. Therefore, the development of device-specific test acceptance criteria is determined for each device as described above. Using the method of determining acceptance criteria of the instant disclosure using the Sentinel Blackbelt Test System from Cincinnati Test Systems, the acceptance criteria of a non-limiting examples of devices is shown in Table 6.

TABLE 6

| Device | Acceptance criteria (95/90 UTL) |
|---|---|
| Biosense Webster PentaRay EP | 109.23 sccm |
| Abbott (St. Jude Medical) Advisor HD Grid | 157.32 sccm |
| St. Jude Medical BRK Transseptal Needle having a length of 71 cm | 175.8 sccm |
| St. Jude Medical BRK Transseptal Needle having a length of 89 cm | 161.1 sccm |
| St. Jude Medical BRK Transseptal Needle having a length of 98 cm | 154.3 sccm |
| Baylis NRG Transseptal Needle having a length of 71 cm | 216.88 sccm |
| Baylis NRG Transseptal Needle having a length of 98 cm | 232.57 |
| Abbott Advisor HD Grid | 157.32 cm |
| Boston Scientific INTELLAMAP ORION ™ Mapping Catheter | 110.760 sccm |

II. Methods of Using Acceptance Criteria

Another aspect of the instant disclosure encompasses an inspection method for accepting a device comprising a lumen as unoccluded or rejecting the device as occluded. The method comprises determining or having determined acceptance criteria for a device representative of the device to be inspected; measuring the flow rate for the device to be inspected; and comparing the mass flow measurement in the device to acceptance criteria determined for an occluded representative device. An inspected device is determined to be occluded if a mass flow measurement for the inspected device is equal to or lower than the acceptance criteria, and the inspected device is determined to be unoccluded if the mass flow measurement in the inspected device is higher than the acceptance criteria. Acceptance criteria for a device representative of the device to be inspected can be determined using a method of Section I. As explained above in Section I(b), acceptance criteria determined using a method of the instant disclosure can be used to determine if a tested device is occluded with particles as small as 50 microns or less, a particle size significantly smaller than a particle size deemed clinically safe. In some aspects, the device comprises one lumen. In some aspects, the device comprises more than one lumen.

Any occlusion in a device to be inspected can be detected using a method of the instant disclosure. A device to be inspected can be a device previously used in the clinic and re-processed for additional use. Alternatively, the device can be a new previously unused device. An occlusion can be an occluding particle acquired in the lumen of the device during clinical use before or after reprocessing of the device. Further an occlusion can be an occluding particle acquired during manufacturing, packaging, shipping, and handling. Additionally, an occlusion can be a defect in the lumen acquired during handling or manufacturing of the device to be inspected. Non-limiting examples of a defect in the lumen of the device include a kink, a manufacturing defect, and a defect in a coating of the lumen.

Another aspect of the instant disclosure encompasses a method of determining if a lumen of a lumen device to be inspected is occluded. The method comprises obtaining or having obtained a mass flow measurement for the device to be inspected; and comparing the mass flow measurement in the device to acceptance criteria obtained for a representative device. The inspected device is determined to be occluded if a mass flow measurement for the inspected device is equal to or lower than the acceptance criteria, and the inspected device is determined to be unoccluded if the mass flow measurement in the inspected device is higher than the acceptance criteria. In some aspects, the method further comprises determining the acceptance criteria of the representative device. Acceptance criteria can be determined using a method described in Section I herein above.

An additional aspect of the instant disclosure encompasses a method of detecting a change in a lumen property of a lumen device. The method comprises obtaining or having obtained a mass flow measurement for the device to be inspected; and comparing the mass flow measurement in the device to acceptance criteria obtained for a representative device. The property of the device is determined to be changed if a mass flow measurement for the device is significantly different from the acceptance criteria, and the property of the device is determined to be unchanged if a mass flow measurement for the device is significantly equal to the acceptance criteria. In some aspects, the method further comprises determining the acceptance criteria of the representative device. Acceptance criteria can be determined using a method described in Section I herein above.

Non-limiting examples of a representative device include an unused originally manufactured device (OM), a used OM device, an unused reprocessed device, or a used reprocessed device, among others. In some aspects, the device is an unused OM device. In some aspects, the device is a used OM device. In some aspects, the device is an unused reprocessed device. In some aspects, the device is a used reprocessed device. A used device can be a device previously used in a procedure once or more, including 2 times, 3, 4, 5, 6, 7, 8, 9, or 10 times or more.

As used herein, the term "change in a lumen property" refers to any change to any part of a device that changes mass flow in the lumen of a device when compared to a representative device. The change in a property of the device could have occurred before manufacture, during manufacture, during shipping and handling, during use, after use but before re-processing, during reprocessing, after reprocessing or any combination thereof.

The change in the lumen property can be a change in dimensions of the lumen, a change in material of the lumen, a change in device-specific parts attached along the fluid flow of the lumen, or any combination thereof. For instance, the change in material of the lumen can include, without limitation, a change in material used to manufacture of the lumen by the original manufacturer, a change in material caused by intended alteration of the device, a defect caused during manufacture, a defect caused during shipping and handling of the device, a defect caused during use of the device, a change in physical characteristics of a lumen resulting from use of the device, or any combination thereof. The polymer used in the manufacture of the lumen of the device can be replaced by the manufacturer, a coating of the lumen can be added or changed by the OM or a reprocessor when compared to the representative device, deterioration of material of the lumen during storage, shipping, and handling, the chemical composition of material of the lumen or the chemical composition of a coating in the lumen can be changed during use of the device or during reprocessing for example by reaction with fluids used during a procedure or during reprocessing, or any combination thereof. Other changes can be recognized by individuals of skill in the art.

The change in the dimensions of the lumen can result from an occlusion in the lumen, a change in the inner diameter and shape, a change in tube curvature, a change in tube length, a damaged lumen, a manufacturing defect, addition of a coating not previously used in the representative device, a damaged lumen, or any combination thereof. Any change in dimensions of the lumen can be caused, without limitation, during manufacture, during shipping and handling of the device, during use of the device, or any combination thereof.

Yet another aspect of the instant disclosure encompasses a quality control method of accepting or rejecting a lumen device before use. The method comprises obtaining or having obtained a mass flow measurement for a manufactured device to be inspected; and comparing the mass flow measurement to acceptance criteria determined for a representative device. The manufactured device is accepted if a mass flow measurement for the manufactured device is substantially equal to the acceptance criteria. The device can be an original manufactured device, a reprocessed device, an altered device, or any combination thereof.

One aspect of the instant disclosure encompasses a method of quantifying the level of occlusion of a lumen of a device to be inspected. The method comprises measuring or having measured change in mass flow through a lumen of a representative device as a function of a change in the level of occlusion of the lumen of the representative device. The method further comprises obtaining or having obtained a mass flow measurement for the device to be inspected; and deriving the level of occlusion of the lumen of the device to be inspected using the measured change in mass flow through a lumen of the representative device. In some aspects, the level of occlusion represents the number of particles occluding the lumen, the size of particles occluding the lumen, or any combination thereof.

Another aspect of the instant disclosure encompasses a method of determining the number of particles in a lumen of a device to be inspected. The method comprises measuring or having measured change in mass flow through a lumen of a representative device as a function of a predetermined change in the number of particles occluding the lumen of the representative device. The method further comprises obtaining or having obtained a mass flow measurement for the device to be inspected; and deriving the number of particles occluding the lumen of the device to be inspected using the measured change in mass flow through a lumen of the representative device.

III. Computer-Implemented Methods and Systems

In one aspect, the present disclosure provides an inspection system for determining if an inspected device is occluded. The system comprises an instrument for measuring mass or volume flow and pressure of a fluid in the lumen of the device for calculating a flow rate in the lumen of the inspected device. The system also comprises a computer system having at least one processor and associated memory comprising acceptance criteria for identification of occluding particles in a lumen of the inspected device and instructions which, when executed by the at least one processor, cause the at least one processor to receive the measured mass or volume flow and pressure in the lumen of the inspected device, calculate the flow rate in the lumen of the inspected device, and compare the calculated flow rate in the lumen of the inspected device to the acceptance criteria, wherein the inspected device is occluded if a calculated flow rate in the inspected device is equal to or lower than the acceptance criteria, and the inspected device is unoccluded if the calculated flow rate of the inspected device is higher than the acceptance criteria. The processor also outputs inspection results for if the inspected device is occluded.

In another aspect, the present disclosure provides a system for determining acceptance criteria for identification of occluding particles in a lumen of a device to be inspected. The system comprises an instrument for measuring mass or volume flow and pressure of a fluid in the occluded lumen of a device representative of the device to be inspected. The system further comprises a computer system having at least one processor and associated memory comprising instructions for calculating an upper test limit flow rate for the representative device using the measured mass or volume flow and pressure in the lumen of the representative device and instructions which, when executed by at least one processor, cause the at least one processor to receive the measured mass or volume flow and pressure and calculate the upper test limit flow rate in the lumen of the representative device, wherein the upper test limit mass flow rate is the acceptance criteria and wherein an inspected device is occluded if a flow rate measurement in the inspected device is equal to or lower than the acceptance criteria, and the inspected device is unoccluded if the flow rate measurement in the inspected device is higher than the acceptance criteria. The computer system also outputs the acceptance criteria, In one aspect, the present disclosure provides at least one non-transitory computer readable medium storing instructions which, when executed by at least one processor, cause the at least one processor to receive mass or volume flow and pressure measurements in the lumen of a occluded device representative of a device to be inspected and calculate an upper test limit flow rate for the occluded representative device, wherein the upper test limit flow rate for the occluded representative device is the acceptance criteria and wherein an inspected device is occluded if the flow rate measurement in the inspected device is equal to or lower than the acceptance criteria, and the inspected device is unoccluded if the flow rate measurement in the inspected device is higher than the acceptance criteria. The instructions also cause the at least one processor to output acceptance criteria for a device to be inspected.

In yet another aspect, the present disclosure provides at least one non-transitory computer readable medium storing instructions which, when executed by the at least one processor, cause the at least one processor to receive a calculated flow rate for an inspected device and compare the calculated flow rate for the inspected device to the acceptance criteria obtained using an occluded device representative of a device to be inspected. The instructions also cause the at least one processor to output test results for accepting or rejecting the device, wherein an inspected device is occluded if the flow rate measurement in the inspected device is equal to or lower than the acceptance criteria, and the inspected device is unoccluded if the flow rate measurement in the inspected device is higher than the acceptance criteria.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred aspects(s) thereof, the articles “a”, “an”, “the” and “said” are intended to mean that there are one or more of the elements. The terms “comprising”, “including” and “having” are intended to be inclusive and mean that there may be additional elements other than the listed elements.

Methods according to the above can be implemented using computer-executable instructions that are stored or otherwise available from computer-readable media. Such instructions can comprise, for example, instructions and data which cause or otherwise configure a general-purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

As various changes could be made in the above-described methods without departing from the scope of the invention, it is intended that all matter contained in the above description and in the examples given below, shall be interpreted as illustrative and not in a limiting sense.

As used herein, the term “occluded device” refers to a device comprising a lumen and having a lumen occluded by one or more occluding particles. An occluded device can be completely or partially occluded by one or more occluding particle. An occluded lumen is partially occluded if a flow of fluid can be detected or measured, whereas a lumen is completely occluded (blocked) if no fluid flow through the lumen can be detected.

As used herein, the term “unoccluded device” refers to a device comprising a lumen and having a lumen clear of any occluding particles.

As used herein, the term “representative device” refers to a device used to determine acceptance criteria for an inspected device.

As used herein, an “inspected device” refers to a device having undergone a flow rate measurement for use in a method or system for identifying occluding particles in the lumen of the device.

As used herein, the term “device,” when not qualified by the terms “inspected” or “representative”, refers to the device for which acceptance criteria are developed, and which undergoes testing for identification of occluding particles in a lumen of the device.

EXAMPLES

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The publications discussed throughout are provided solely for their disclosure before the filing date of the present application. Nothing herein is to be construed as an admission that the invention is not entitled to antedate such disclosure by virtue of prior invention.

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1. Development of Mass Flow Method of Identification of Occluding Particles in Microlumens An in-process inspection testing method capable of detecting and rejecting devices with microlumens containing unacceptable levels of clinically relevant particles is presented herein.

By adapting current leak testing technology, validated for use in nearly every field, including medical, a mass flow inspection test that is capable of identifying a single small particle within a microlumen was developed. Further, investigation also showed that this method could repeatedly identify a wide range of particle quantities, allowing a full scale to be developed by which occlusions (partial or otherwise) could be graded. This test method is intended to create a new standard by which manufacturers of medical devices containing small lumens should consider when attempting to mitigate periprocedural patient risk.

Introduction.

Performed to diagnose and treat most arrythmias, an EP study utilizes specialized catheters, introducers, and other complex technologies. These devices are most often inserted via venous (femoral) access and delivered to the right atrium, with a transseptal puncture providing access to left-sided anatomy as necessary. Most studies are routine, completed in a few hours, and the patient can be expected to resume normal daily activities within just a few days. However, with an elementary understanding of anatomy, concern arises that devices placed within cardiac chambers could release potentially embolic particulates. Those discharged into the right side of the heart could occlude pulmonary arterioles (average diameter <300 micron) if large enough, potentially resulting in a pulmonary embolism (PE). Left-sided studies could direct emboli to the brain, potentially resulting in a CVA. Occlusion of penetrating arterioles (average diameter <100 micron) is of greatest concern, inducing more traumatic neuropathy.

A contributing factor to these complications results from potentially embolic particulates either on, in, or created by, a device, fluid, or other object introduced into the patient. The consequences of particles delivered into the bloodstream have long been understood. But, while catheters have been used for EP studies for decades, there exists no single, well-defined standard for particulates on or in an EP catheter, or related, by which manufacturers of such devices must adhere. Many default to those drafted by the United States Pharmacopeia (USP), particularly the direction found in General Chapter <1> Injections and Implanted Drug Products. This chapter focuses on parenteral drug products that are injected or implanted into the body. It further points to other chapters that define additional testing requirements unique to the many different materials considered. The chapter commonly referenced by catheter manufacturers when discussing particulate acceptance criteria is <788> Particulate Matter in Injections. This chapter defines acceptable particulate sizes and quantities in injectables, and the test methods used to characterize them. Here, acceptance criteria focus on larger amounts (600 or 6000) of smaller particulates (25 or 10 micron, respectively). The clinical concern is that patients often receive multiple injections of various required solutions during their care. It has been estimated that a patient in intensive care is injected with as many as a million particles larger than 2 micron every day of their stay. While lesser amounts of smaller particles may not be acutely traumatic, cumulative doses of smaller particulates has proven deleterious. For example, parenteral nutrition solutions have been shown in the past to include nearly 40,000 particles upwards of 100 micron each in daily feedings, with little to no acute risk. However, prolonged administration allows for the accumulation of fatal quantities of particles. Because of this, minimizing the quantity of smaller particles in each injection, either via implementation of inline filters and/or improved manufacturing techniques, will reduce the overall load a patient experiences, abating risk of further embolic complication.

Additional governance is provided by USP regarding perfusion scintigraphy studies, recommending the majority of particulates involved be around 90 micron in diameter (ranging from 20-150 micron), with none larger than 150 micron. It has been shown that smaller particles (<40 micron) may pass through the vasculature of interest and travel to, and become lodged in, unintended sites potentially leading to delayed disfunction after a critical load has been administered, while larger particles (>200 micron) may block arteries and arterioles, resulting in acute focal defects.

Both the Association for the Advancement of Medical Instrumentation (AAMI) and the Food and Drug Administration have released several guiding documents, such as TIR42 (AAMI) and "Guidance for Coronary, Peripheral, and Neurovascular Guidewires" (FDA), among others. These are similar to USP<788> in that they recommend the characterization of certain sizes of particulates that may originate from the medical devices each is focused on but stop short of defining quantity and size acceptance criteria. This is mostly due to the fact that there is an understandable lack of research involving human subjects given the ethical concerns involved. These documents instead rely on the many related studies employing animal models. While direct correlation is confounded by differences in anatomy, basic principles apply and are intended to aid each manufacturer in defining their own acceptance criteria.

In addition to device-attributed particulates discharged into the vasculature, there is also a concern about potentially embolic-free circulating particulates created during an EP study, especially those procedures involving ablation of intracardiac surfaces. Several studies have identified asymptomatic cerebral lesions via MRI following ablation procedures, leading to a presumed direct correlation between ablation procedures and the production of emboli. A recent pair of studies, sponsored by Medtronic, considered the effect of microembolic materials (either air bubbles or pulverized dried blood) created during ablation in the left atrial chamber on canine and porcine models.

The first study investigated the production of microbubbles and embolic particulates during pulmonary vein (PV) ablation in porcine subjects using two specific catheters (Biosense Webster and Medtronic). In this study, microbubbles, and coagulum (averaging 225-250 micron depending on the catheter used) were identified and attributed to the use of the devices, but no evidence of acute cerebral lesions was observed in any of the six participant animals. 73 micron extracorpeal filters were used to collect debris, allowing all smaller debris to continue circulation. In two of the animals, renal arterial occlusion was present with subsequent tubular necrosis, but no other lesions or dysfunction was reported elsewhere.

In the second study, over 4000 particulates or a quantity of microbubbles were injected into a canine subject in four doses (4 injections of >1000 particles, or up to 4 injections of 0.5 mL of microbubbles). Several ranges of sizes were considered, from 75-250 micron to 90-600 micron. The effects of introducing single particles or microbubbles of any size were not studied. Nor were the effects after introducing a quantity of particles of a single size. The location of the injection (vertebral vs carotid sinus) and the size of the particulates directly correlated with increased severity of the outcome.

In both studies, as in several others before and since, a significant load (quantity $10^3$-$10^6$) of larger embolic (>>>50 micron) particles were required to cause injury. Studies on atheroemboli to the brain have shown a remarkable acute tolerance of considerably large emboli (50-300 micron) by the cerebral vasculature, likely due to redundant blood supplies caused by arterial anastomoses and arteriovenous shunts. Considering the other end of the spectrum, an oft-cited work by Heistad, et al., studied the injection of nearly 30,000 smaller beads (15 micron) into a dog model. He repeated these injections 25 times, observing no ill effects or neurologic deficits. However, when he injected a similar quantity of 50 micron beads, altered blood flow was observed after a single dose. Together, this reinforces the earlier conclusion that fewer larger particles can be more harmful than an even greater quantity of smaller particles, and that multiple ($>10^3$) particles in the arteriole size range and smaller are required to induce significant injury.

Manufacturers of EP products and reprocessing outfits have a shared goal to reduce periprocedural patient injury, especially emboli. As such, good manufacturing practices include methods that specifically minimize and/or remove particulates on or in these products. During reprocessing, adequate inline inspection should be performed on each device, rejecting those that contain an unacceptable level of particulates. This is a relatively routine task when patient contacting surfaces are visible on the exterior of the device. Low level magnification allows for detection of particles that could be of concern. Unfortunately, this becomes significantly more complicated with devices that contain lumens, especially when they are inaccessible. Visualization solutions exist for macrolumens, but more specialized testing must be developed and validated for microlumen products. The testing methods that follow discuss a novel approach to identifying clinically relevant levels of particulates within microlumens of EP devices.

Test Method Development

The test to identify occluded devices relies on standard principles of fluid dynamics and physics where:

$$\text{Flow}(Q) = \frac{\text{Quantity }(g)}{\text{Time }(t)} \qquad \text{Pressure}(P) = \frac{\text{Force }(F)}{\text{Area }(A)}$$

A lumen can be charged to a certain pressure with air, and then air can be delivered through the lumen at a rate required to maintain that pressure. Impacted by the cross-sectional area of the blockage, a fully occluded device will allow little to no quantity (ΔAQ=0) of gas to exit the lumen, thereby requiring little to no additional flow of air to maintain the charge pressure. Non-occluded devices will allow full and rapid flow of gas exiting the lumen, as there is no impedance other than that provided by the properties of the lumen itself (i.e., material, geometry, surface finish, etc.). This will require a much higher flow of air to maintain the charge pressure (FIG. 1). Partially occluded devices will impede this flow to the degree by which they are obstructed as defined in the standard mass flow equation below, requiring a flow of air between that required for the fully and non-occluded devices.

$$\Delta Q = \frac{\pi \Delta P d^4}{128\ \mu l}$$

This testing is commonly referred to as mass flow testing. It is ideally suited for use with microlumens because it is capable of grading the degree of blockage, which is necessary for detecting partial occlusions caused by small particles. Other pressure-based methods are designed for detecting only higher levels of occlusion, so are poorly suited for this application. The addition of a mass flow transducer along with the pressure sensor provides the added sensitivity necessary to ensure that only acceptable levels of particles remain on a device.

The mass flow testing was conducted using a Cincinnati Test Systems (CTS) Sentinel Blackbelt Test System. It utilizes clean, dry, pressurized air to create positive pressure inside a device and provides constant timed flow, which is then sensed by mass flow transducers accurate to 0.5% of full scale (248 sccm scale=±1.2 sccm error). Data is displayed at a 0.00001 resolution.

Development of this test method involved an assessment of the ability of the test method to distinguish between different sized particles as well as different quantities of similar sized particles. This established both a sensitivity range and determined if the instrument was capable of detecting a particle smaller than that deemed clinically relevant. Developing the method to detect a particle smaller than that deemed clinically relevant provides for a safety factor, rejecting devices containing such small particles. Based on the review of literature, and discussions with the FDA, a particle size of 50 micron was chosen for establishing acceptance criteria.

Figure 8:
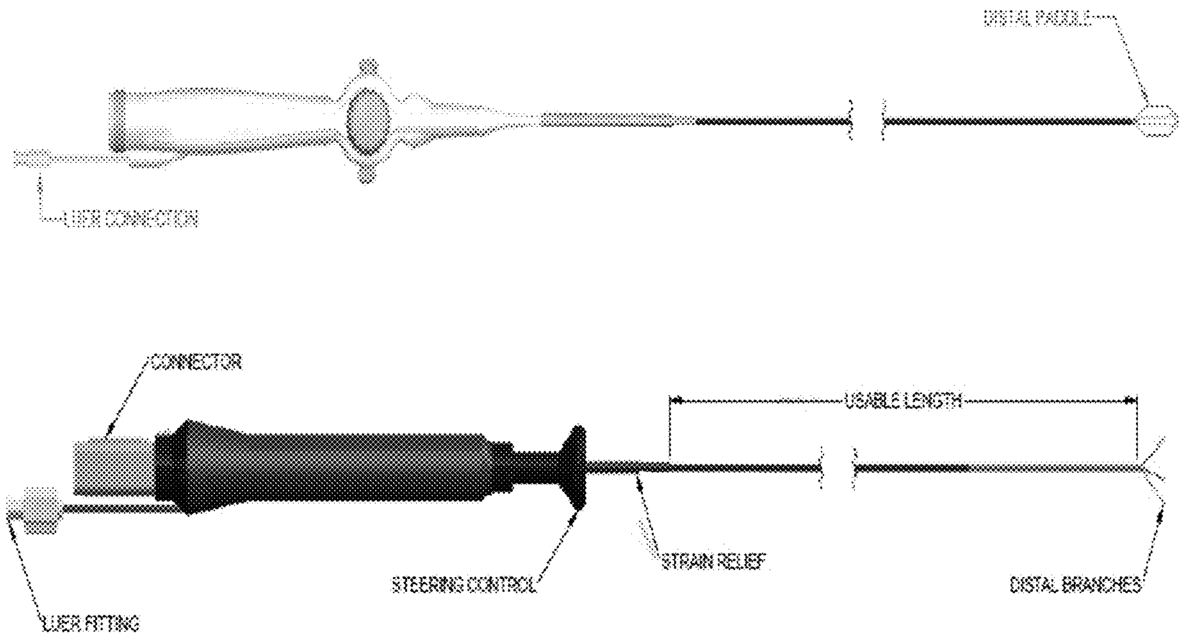
FIG. 8. Design characteristics of the Advisor HD Grid (right) and PentaRay (left catheters.
Figure 9A:
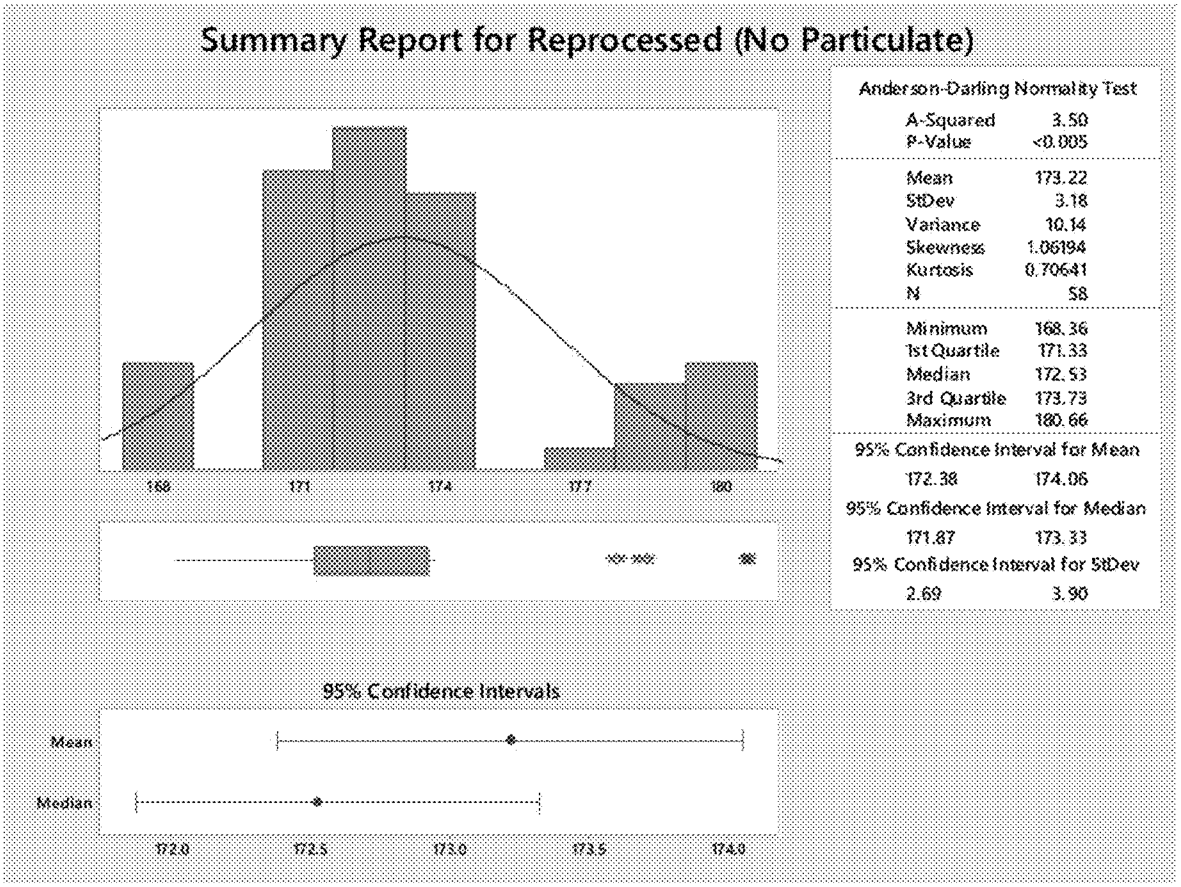
FIG. 9A depicts a summary report for reprocessed (No Particulate) Advisor HD Grid Mapping Catheter devices.
Figure 9B:
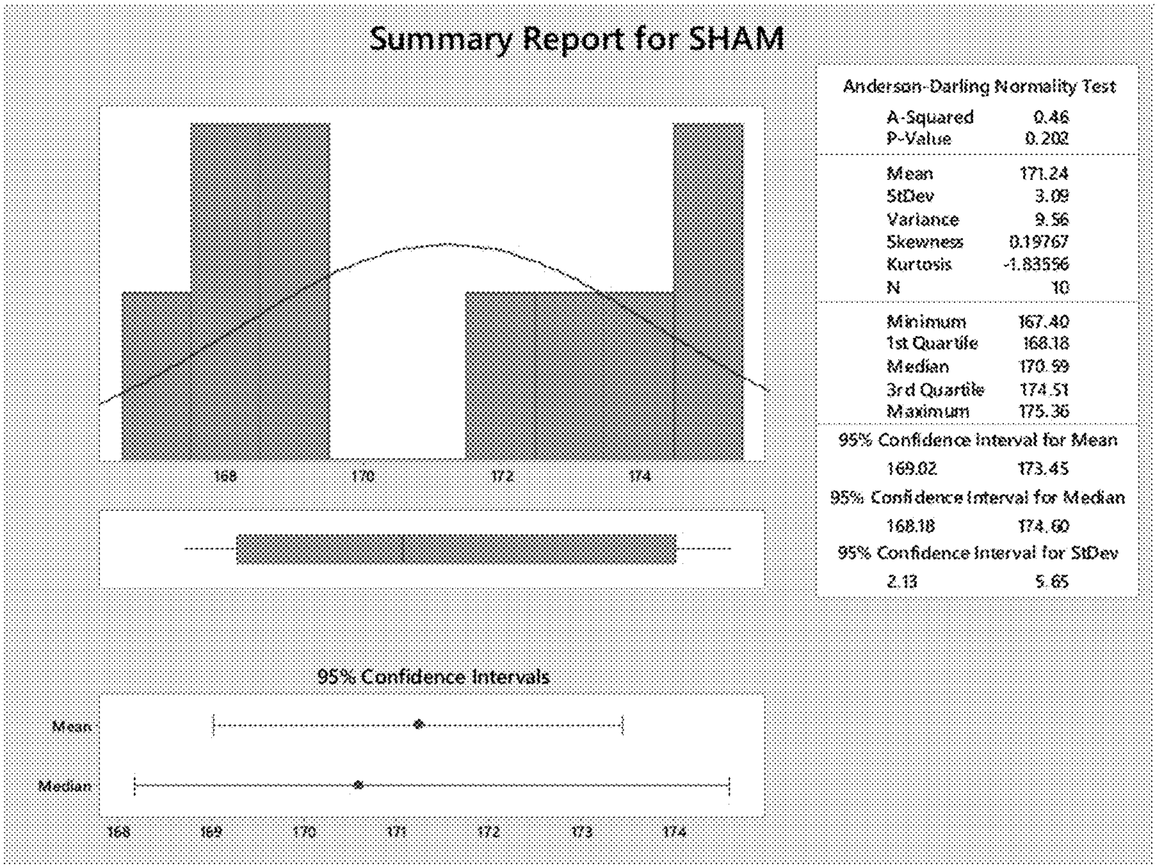
FIG. 9B depicts a summary report for Sham Advisor HD Grid Mapping Catheter devices. Sham devices were inoculated with the bead buffer (carrier) solution only.
Figure 9C:
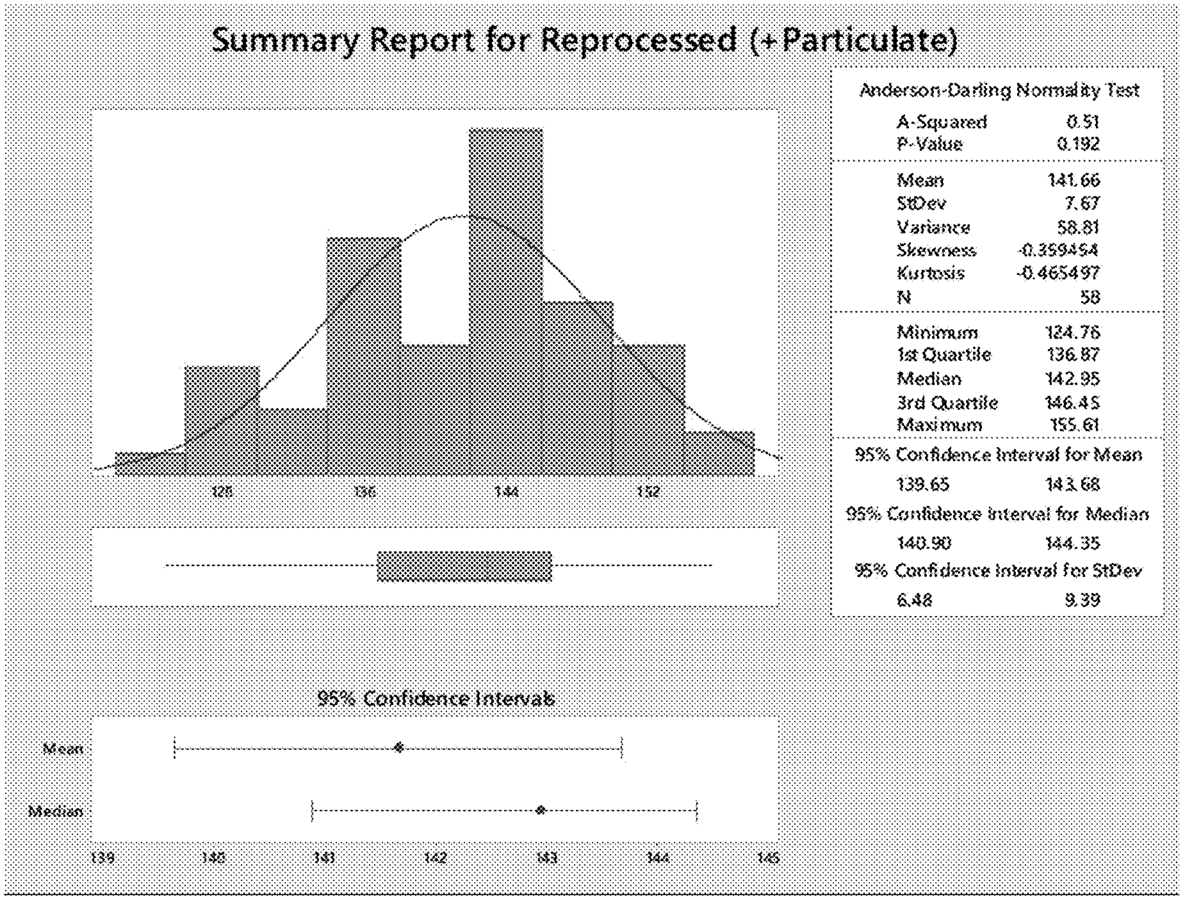
FIG. 9C depicts a summary report for reprocessed (+Particulate) Advisor HD Grid Mapping Catheter devices. Occluded devices were inoculated with a single 50 μm bead.
Figure 10:
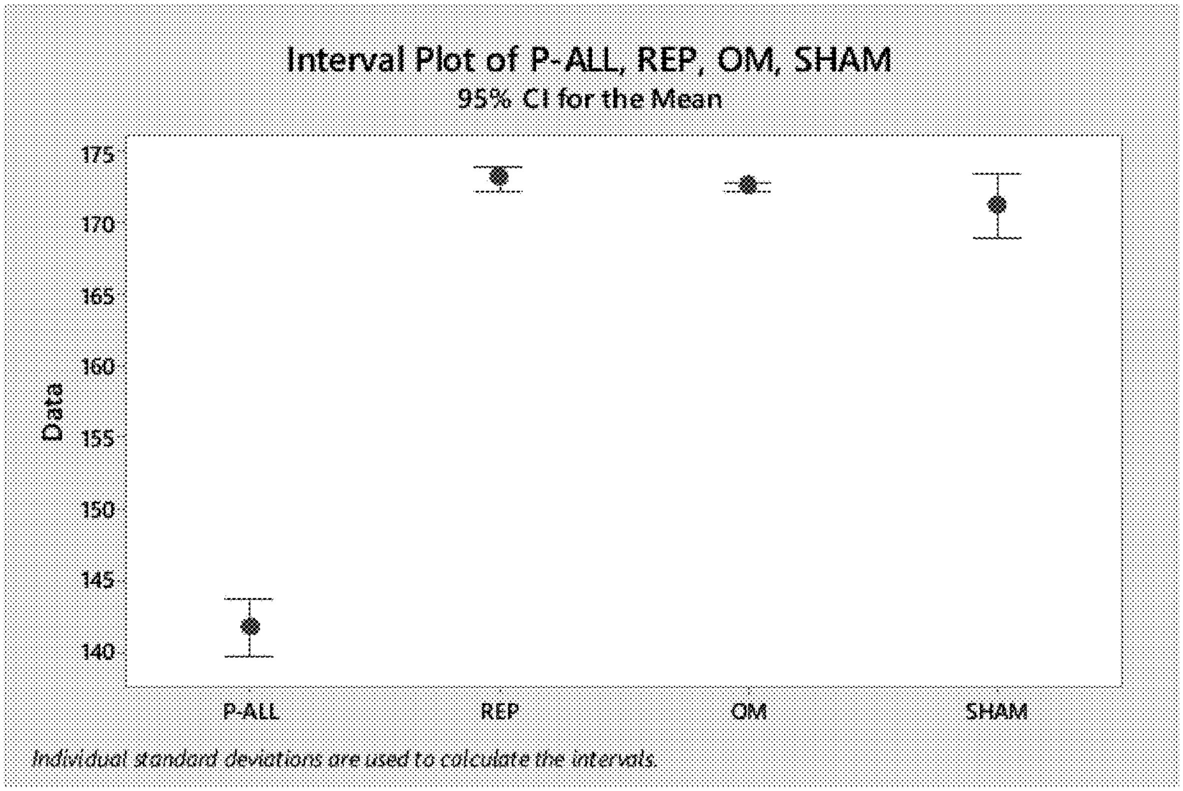
FIG. 10 depicts an interval plot displaying minimal differences in flow between non-occluded OM, Reprocessed, and Sham inoculated devices, but a significant drop in flow between all those sample sets and the devices occluded with a single 50 μm bead.
Figure 11:
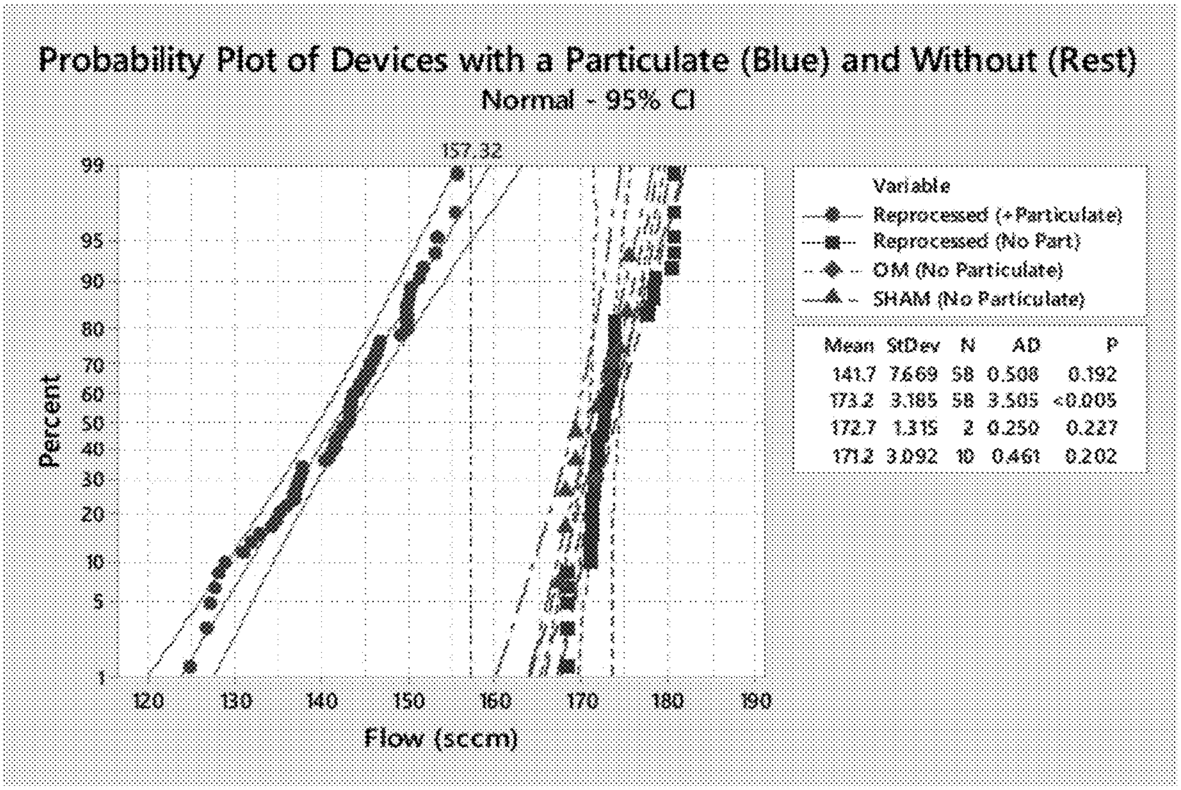
FIG. 11 depicts the upper boundary of the probability plot at 95/95 confidence interval for the devices occluded with a single 50 μm bead is 157.32 sccm. It is also noted that the OM devices perform in a similar manner to reprocessed devices (both without particulates). The sham readings display no significant impact of the carrier fluid on the flow rate (post incubation).
Figure 12:
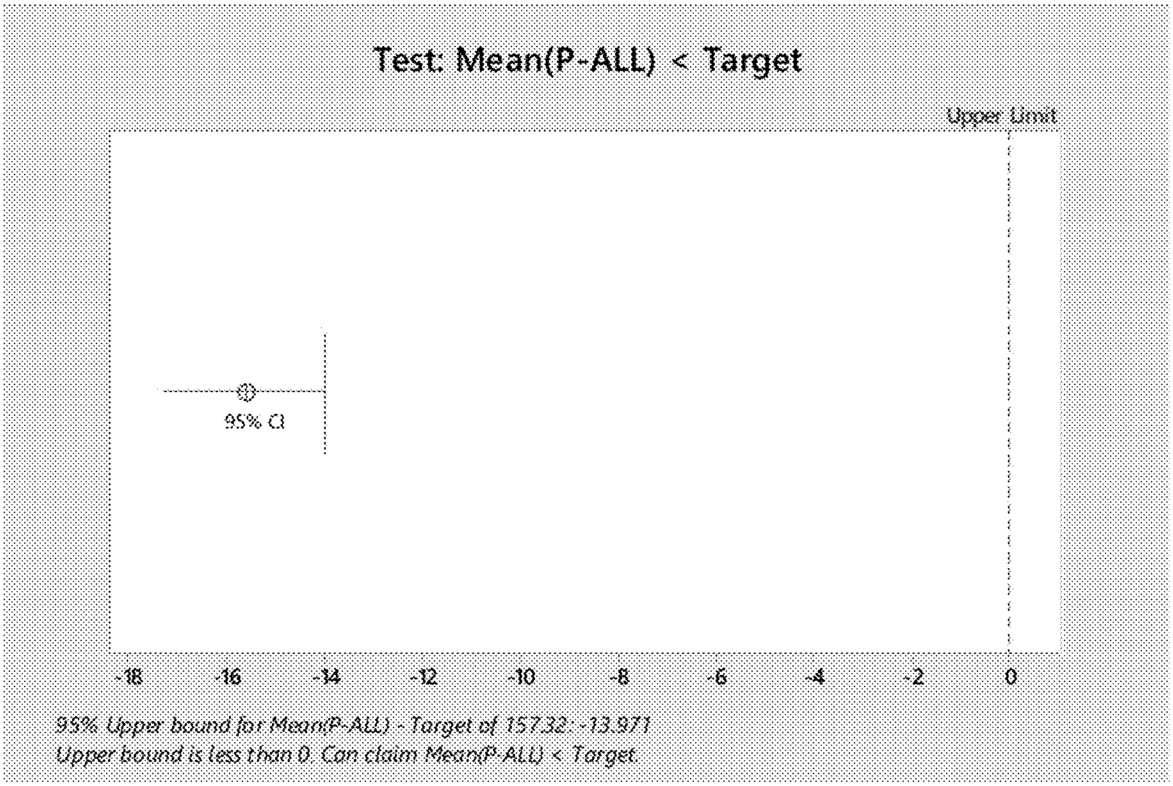
FIG. 12 depicts an equivalence test showing a significant difference between the mean of all occluded samples and the acceptance criteria of 157.32 sccm, and also between the mean of all reprocessed (non-occluded) samples and the acceptance criteria.
Figure 13:
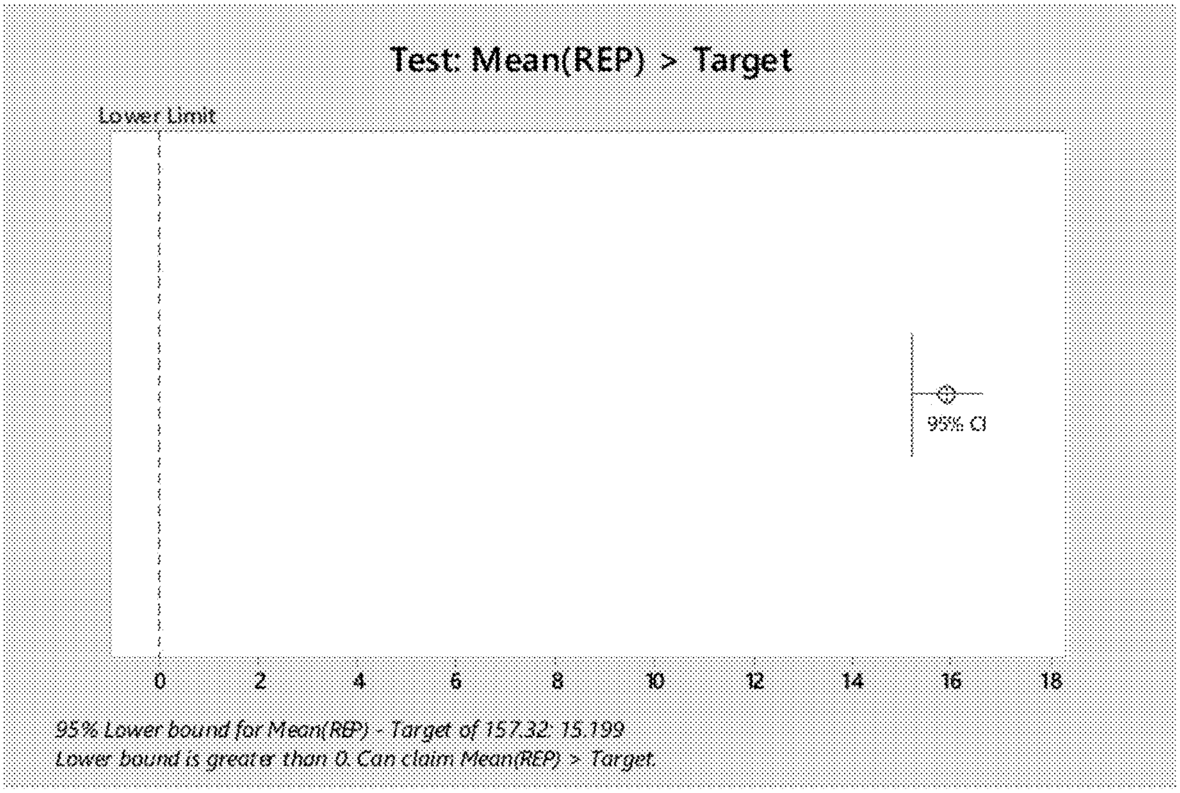
FIG. 13 depicts a distribution plot, which assumes an infinite sample set, suggests the 95/95 acceptance criteria of 157.32 sccm approaches 95/98.
Figure 14:
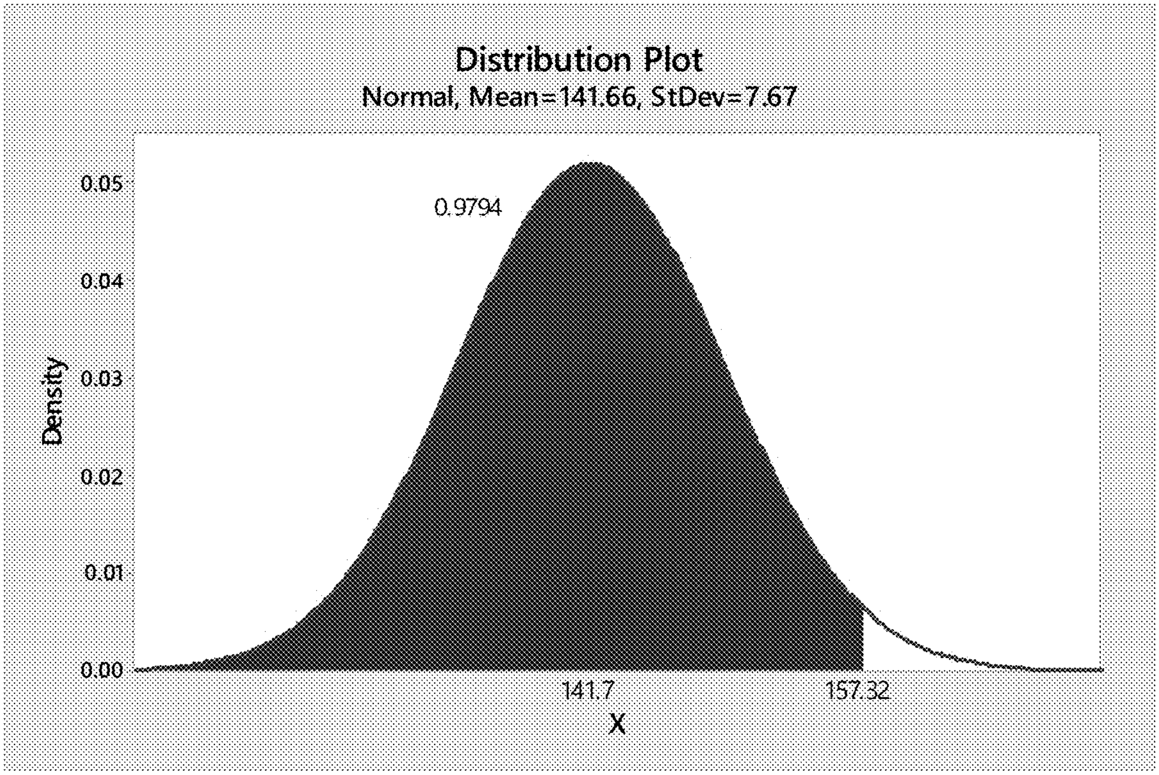
FIG. 14 is a probability distribution plot of samples containing a single 50 μm bead. With system error, the test acceptance criteria approximates 95/98.
Figure 15A:
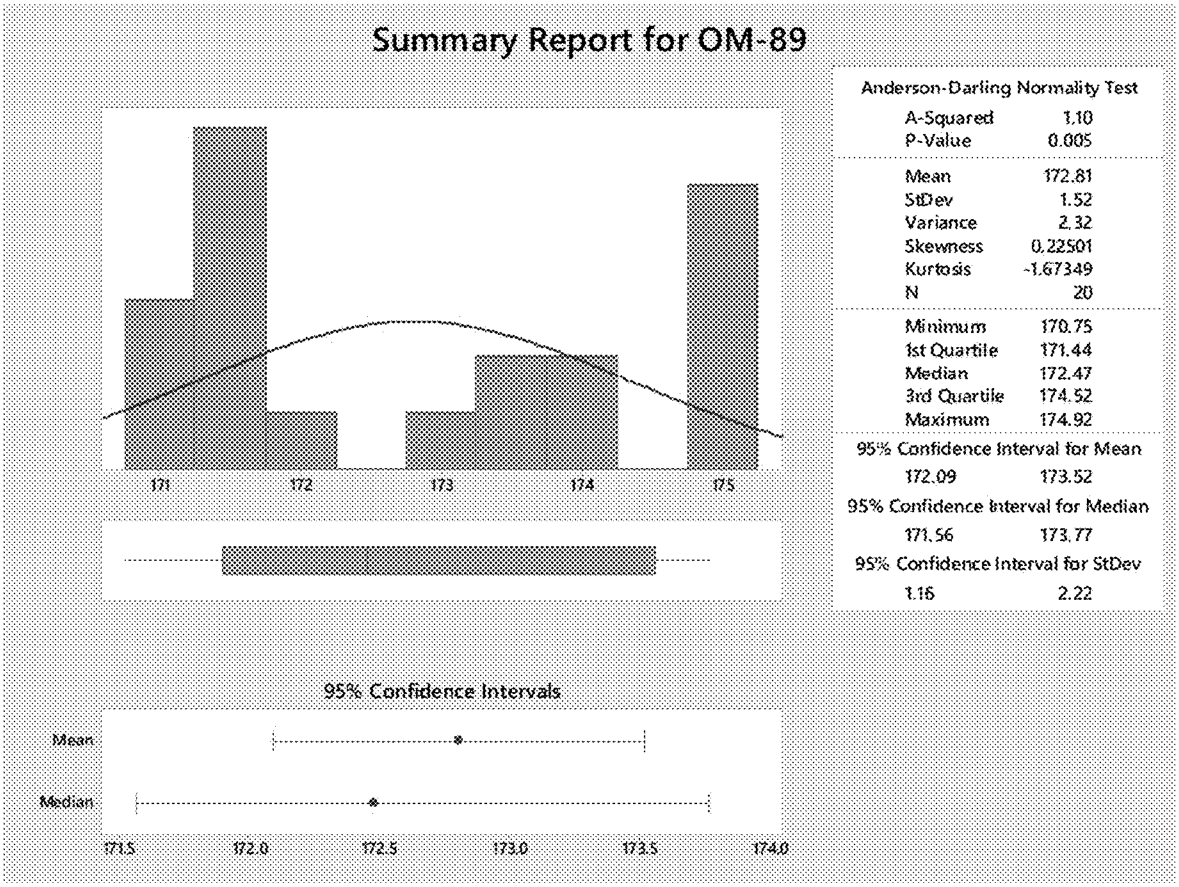
FIG. 15A depicts a summary report for reprocessed (No Particulate) devices.
Figure 15B:
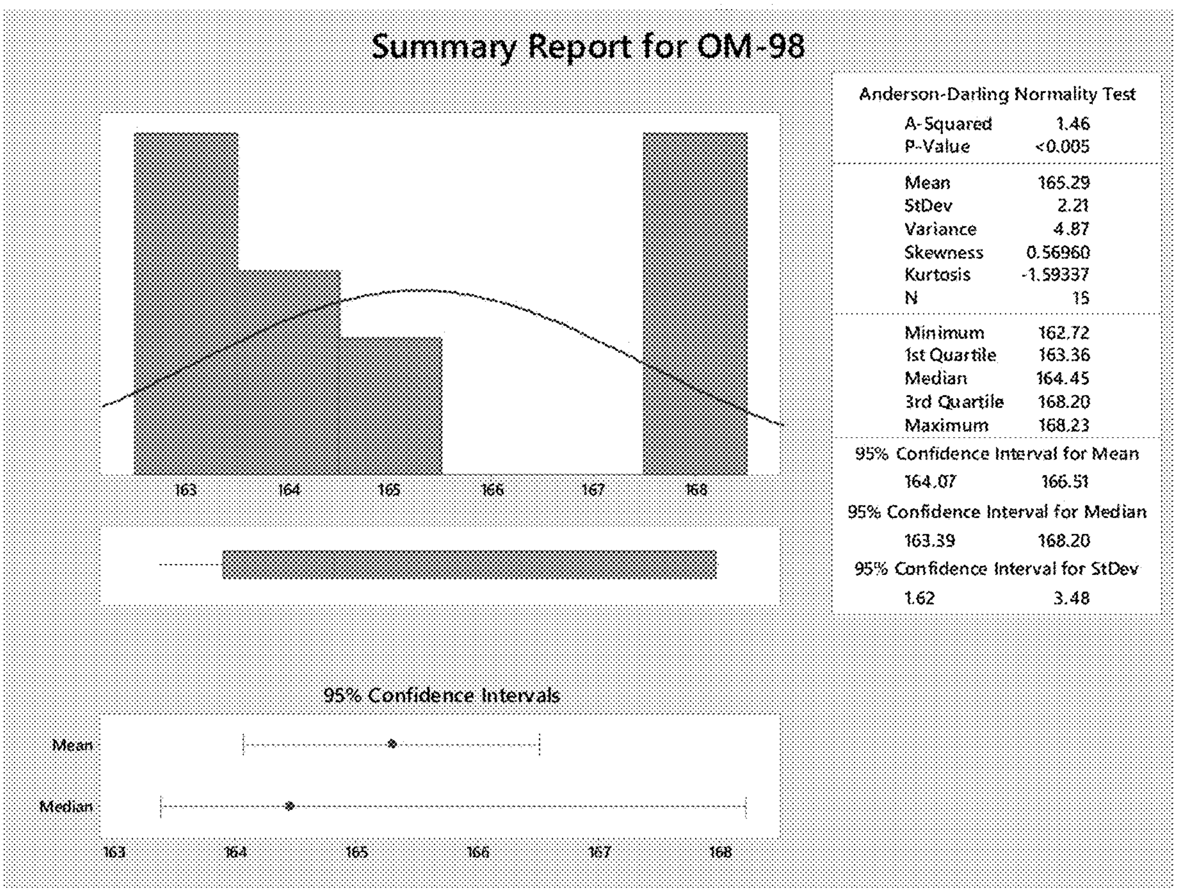
FIG. 15B depicts a summary report for reprocessed (+Particulate) devices. Occluded devices were inoculated with a single 50 μm bead.
Figure 15C:
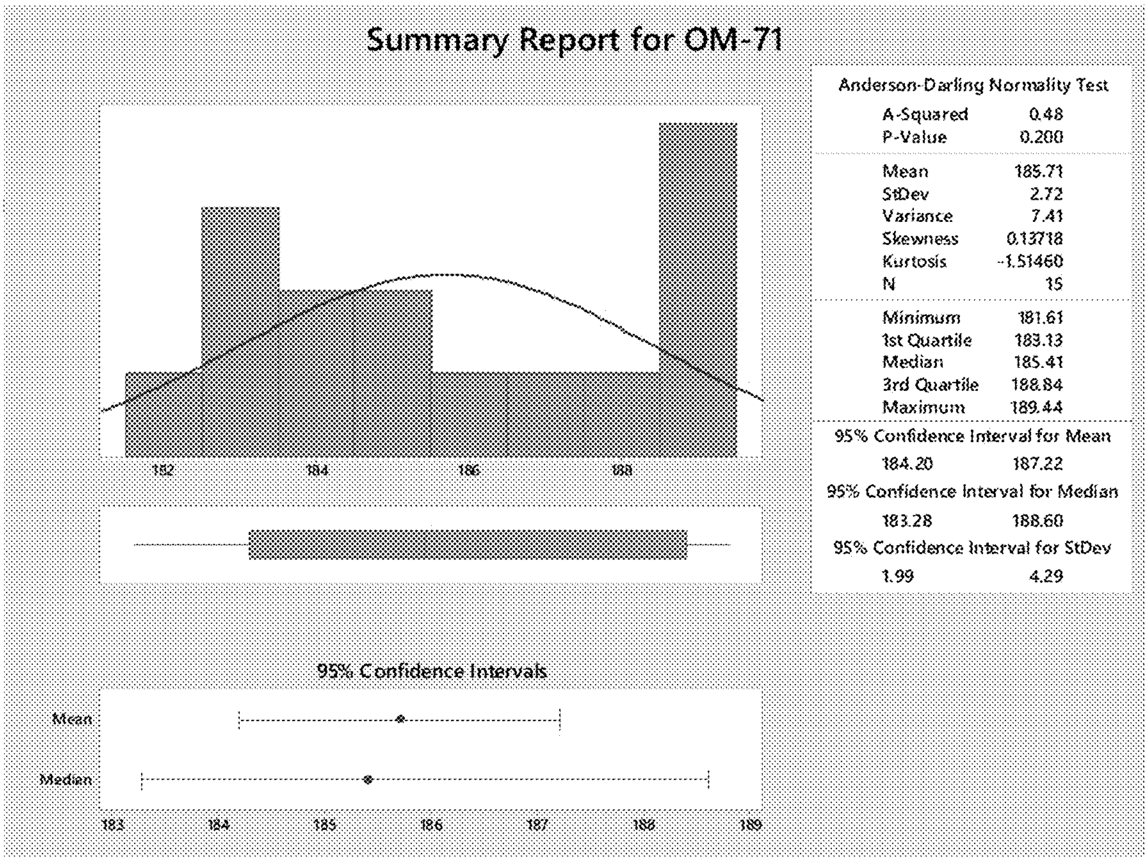
FIG. 15C depicts a summary report for Sham devices. Sham devices were inoculated with the bead buffer (carrier) solution only.
Figure 16:
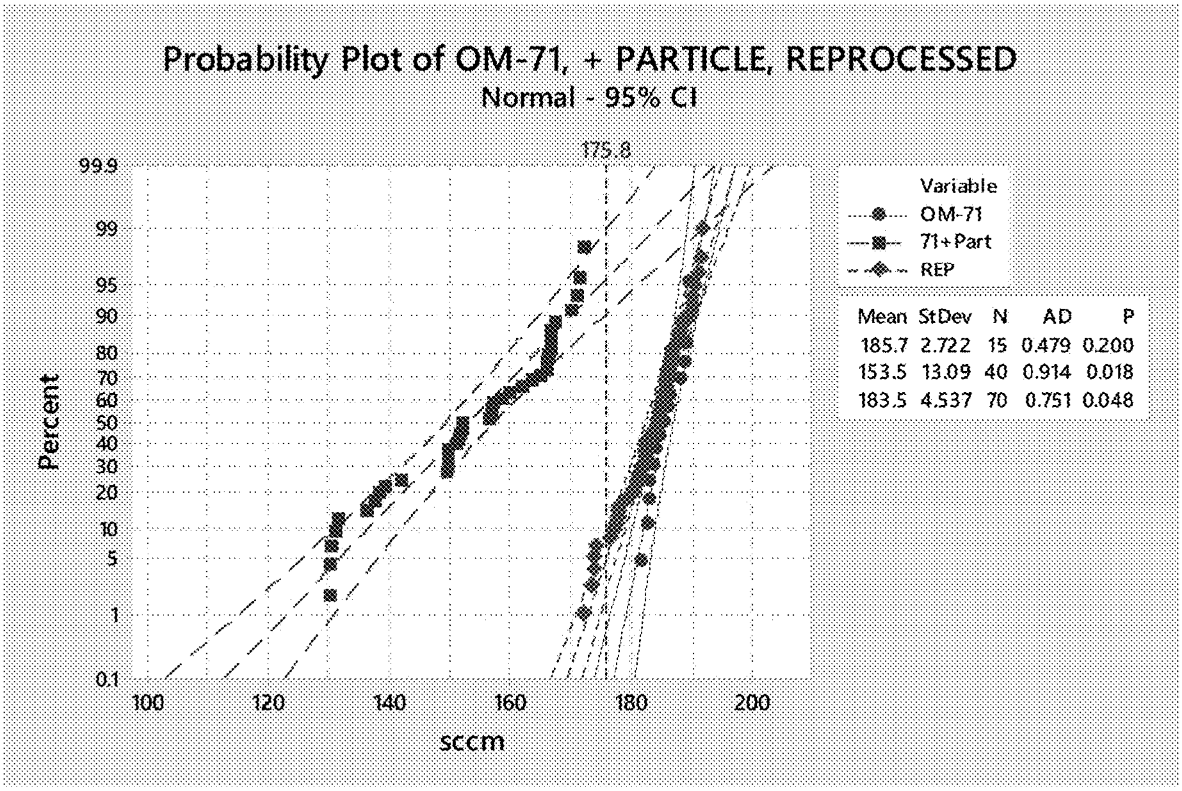
FIG. 16 shows the mass flow rates for 71 cm OM and Reprocessed devices without an occluding particulate and reprocessed devices inoculated with an occluding particulate. The +Particulate 95/90 upper test limit (UTL) flow rate is shown, defining the acceptance criteria for 71 cm needles.
Figure 17:
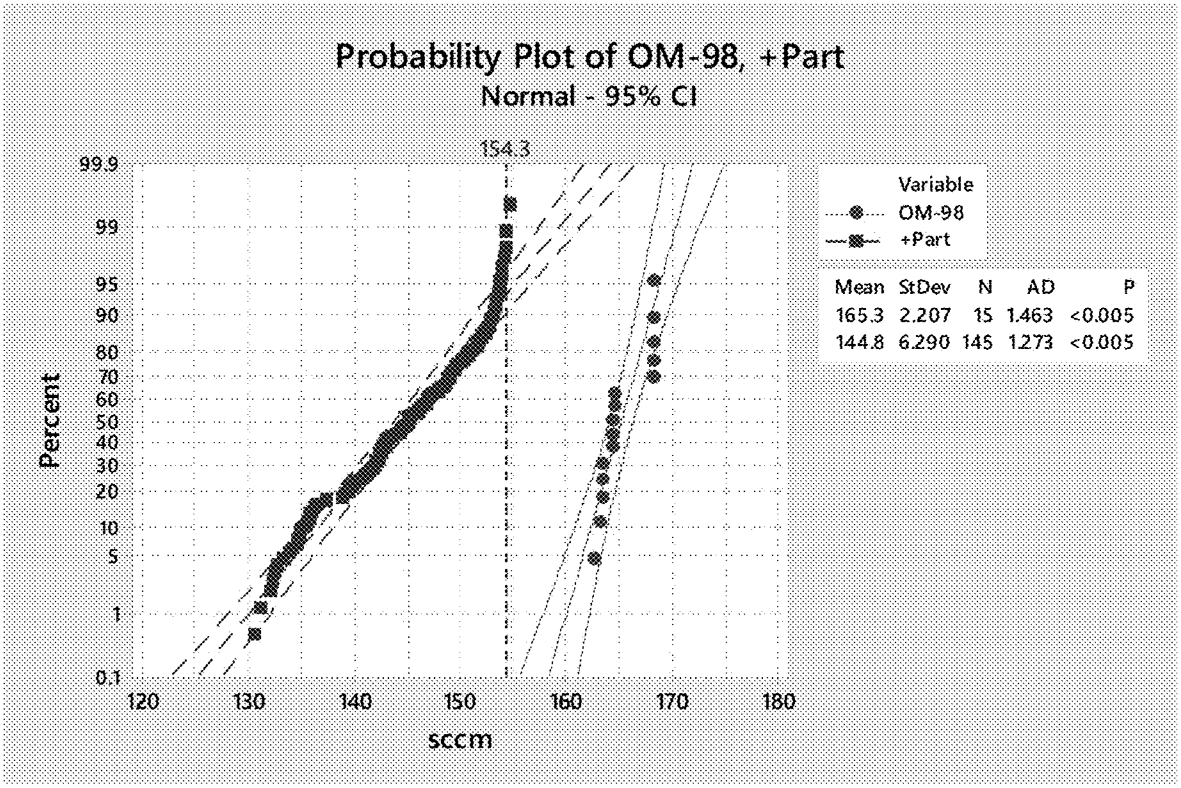
FIG. 17 shows mass flow rates for 98 cm original manufacturer (OM) devices without an occluding particulate and reprocessed devices inoculated with an occluding particulate (+Part). The occluded 95/90 UTL flow rate is shown, defining the acceptance criteria for 98 cm needles.
Figure 18:
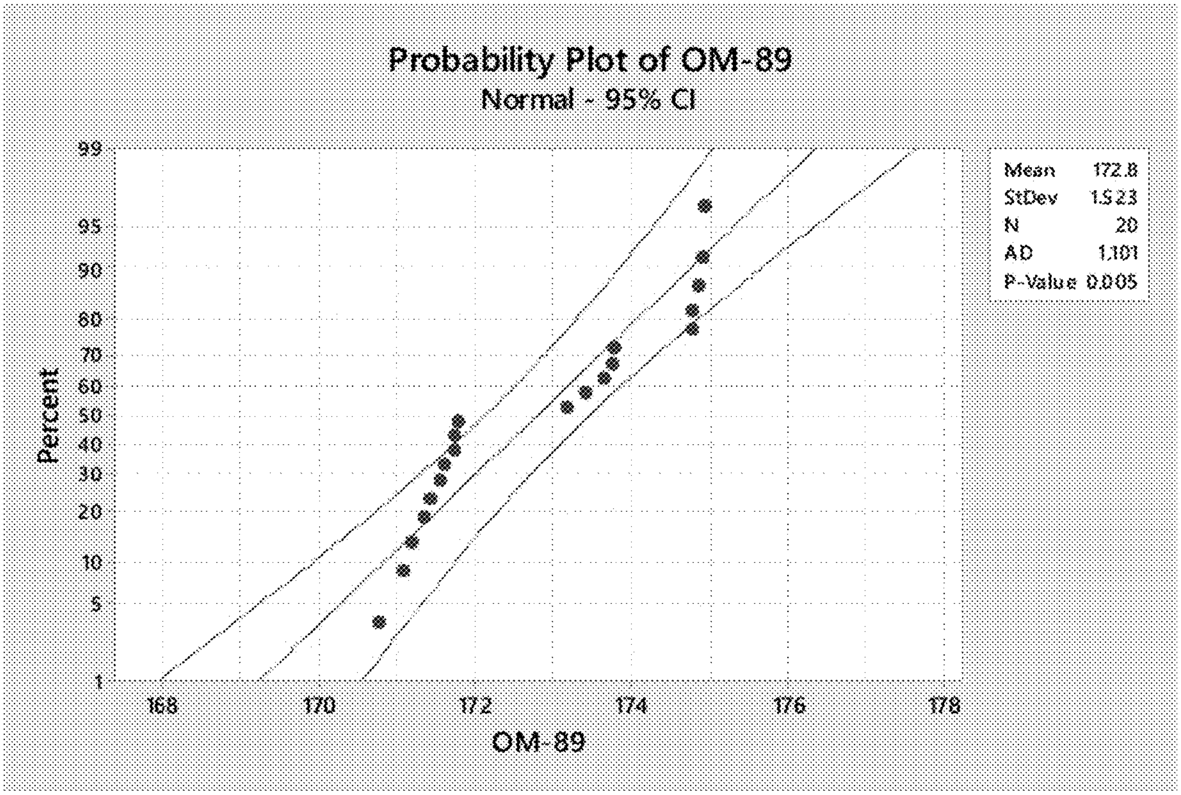
FIG. 18 is a distribution plot of OM mass flow characterization of the 89 cm needle.
Figure 19:
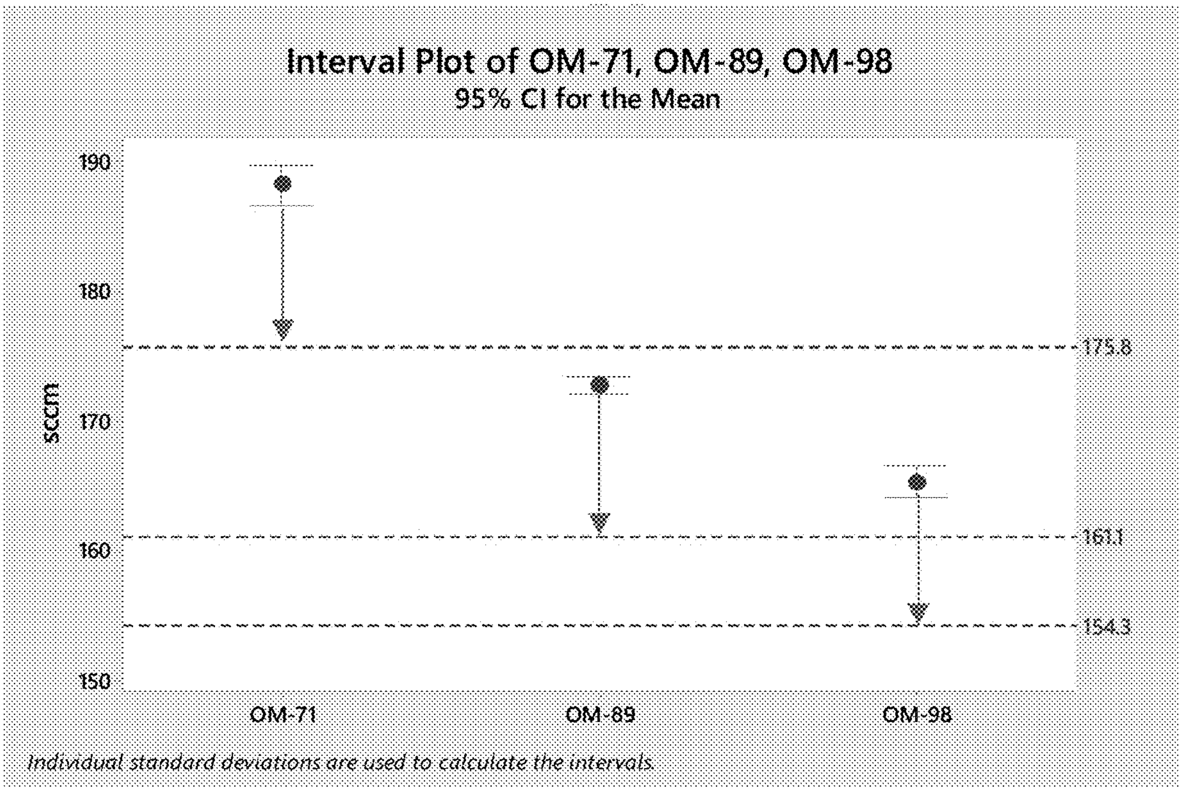
FIG. 19 are the mass flow rates for each OM size needle, with calculated acceptance criteria. For 89 cm needles, the acceptance criterion was derived from the average difference between OM 71 cm and OM 98 cm data and respective acceptance criteria.

The Mass Flow method described herein will be used to establish the test settings for in-process inspection of microlumen devices using the CTS Sentinel Blackbelt test system. The microlumen device used herein is a reprocessed Biosense Webster PentaRay EP catheter. Design characteristics of the device are shown in FIG. 8 (left).

Methods

To define the parameters of the test method, occlusions were created by injecting 50 micron NIST traceable particle size standard polystyrene beads, suspended in bead solution containing ultrapure water, a dilute (<0.2%) aqueous polymeric adhesive and surfactant (<0.5%), into the lumen of each device and allowed to disperse throughout. The surfactant was included to prevent agglomeration in solution while the adhesive was used to lightly adhere the beads to the lumen wall following evaporation of the bead solution. Samples were oven incubated, removing residual moisture that could confound the data.

Control devices included unchallenged original manufacturer devices (OM), unchallenged reprocessed devices (REP), and reprocessed devices with bead solution (SHAM) containing no particles.

Solutions were prepared containing either $10^4$, $10^3$, 500, 100, 50, 5, 2, or 1 (per 100 µl solution) 50 micron bead(s). These were injected into the lumen of three devices per quantity (24 total samples with beads).

All samples were tested 5 times and the flow data recorded in standard cubic centimeters per minute (sccm).

Results

Data was recorded and analyzed in Excel (Microsoft Office 365) and Minitab 18. All statistical analysis was completed in Minitab 18 using the Smallest Extreme Distribution where applicable.

Control samples were tested, as shown in FIG. 1. There was no statistical difference between REP and SHAM devices. The OM devices performed over a lower and wider range, suggesting an artifact of the manufacturing process that is removed during reprocessing (or stretching of the lumen to a uniform diameter following clinical use of pressurized heparinized saline and subsequent reprocessing).

Figure 2:
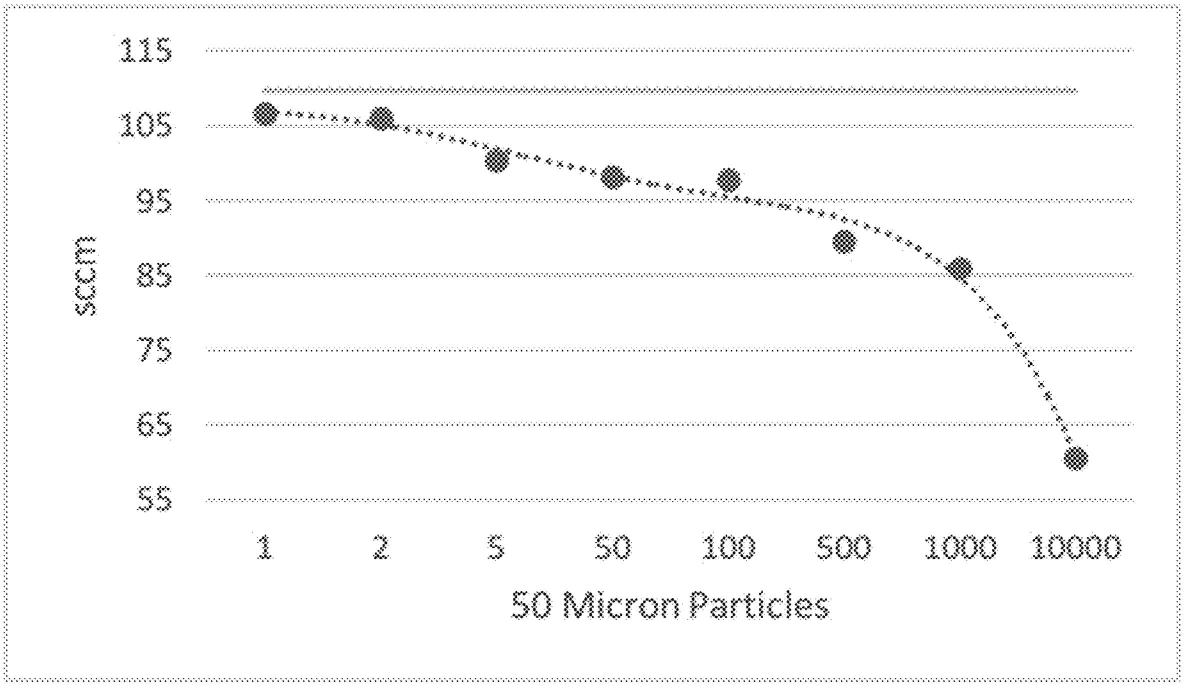
FIG. 2 is a graph showing the flow rate in sccm in devices loaded with an increasing number of 50-micron particles.

The average mass flow decreased (blue) as the quantity of particles increased, as expected, confirming that additional particles further occlude the lumen (FIG. 2). The yellow line reports the average data from the control samples, which proved significantly higher than any of the challenged devices. The average control device had a mass flow reading of 112.01 sccm, whereas the single particle challenged device averaged 106.68 sccm. This data also confirms that the mass flow test on the CTS Sentinel Blackbelt, as designed, is capable of detecting a single 50 micron particle.

Figure 3:
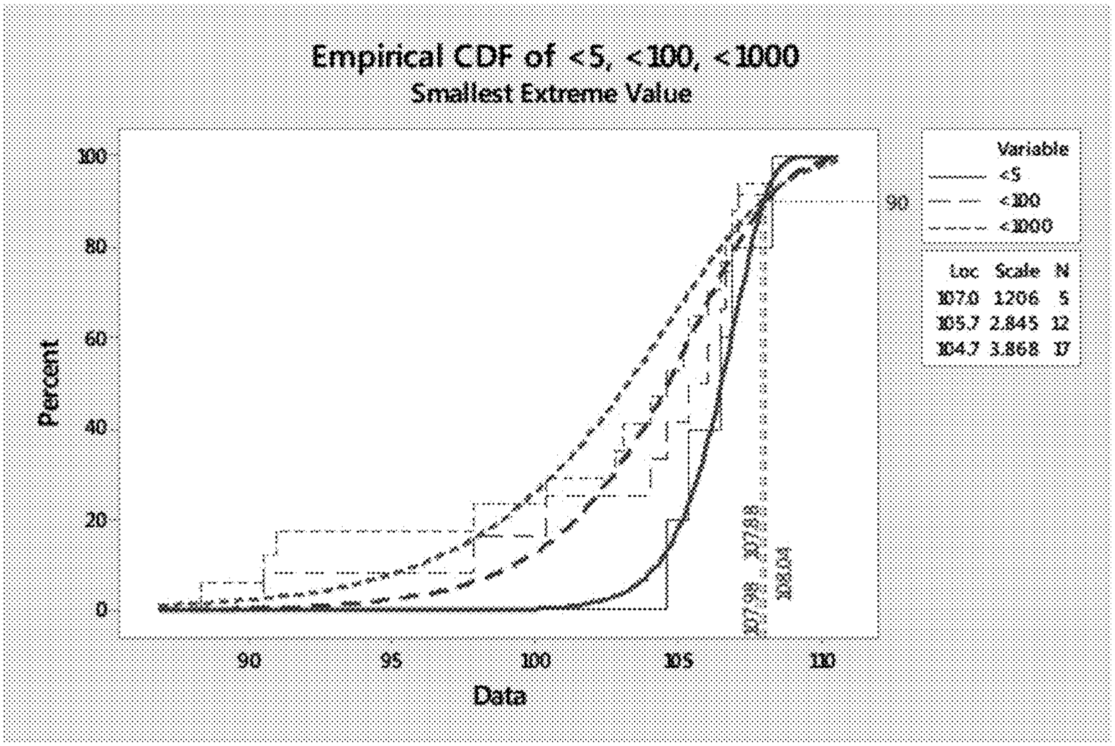
FIG. 3 depicts a cumulative distribution function (CDF) graph of grouped mass flow readings. Samples were grouped by devices containing less than 5, less than 100, and less than 1000 particles. Values displayed are the test limit parameter at 95/90 for each particular group, approximating 108 sccm.
Figure 4:
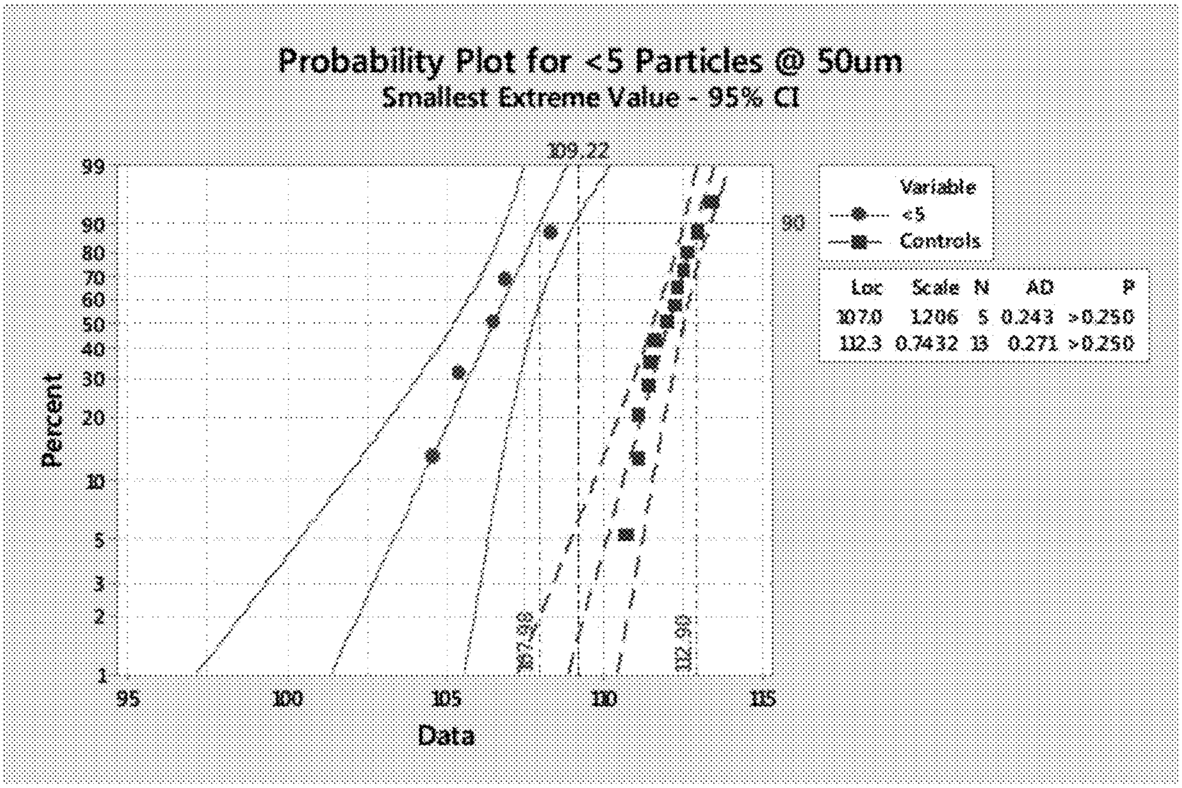
FIG. 4 is a probability distribution plot for flow rates from devices containing 5 or fewer particles, and the control devices. The 95/90 values are shown, along with the calculated test limit value (109.22 sccm; dashed vertical line at 109.22 sccm) incorporating system error of 0.5% of full scale (1.24 sccm).

A cumulative distribution function (CDF) was calculated from grouped flow rate data. Devices were grouped by those containing less than 1000 (N=17 devices), less than 100 (N=12 devices), and less than 5 particles (N=5 devices), and the 95/90 confidence interval test limits are shown, nearing 108 sccm (FIG. 3). The test limit parameter at 95/90 for each particular group, approximated 108 sccm. A probability plot focused on the group of devices containing 5 or fewer particles and compared them to the control devices (FIG. 4). The 95/90 values are shown, with the red line at 109.22 sccm incorporating in system error of 0.5% of full range, establishing the suggested test acceptance criteria. It is noted that this value is above the upper bound at 95/90, providing even more confidence to this defined parameter.

Figure 5:
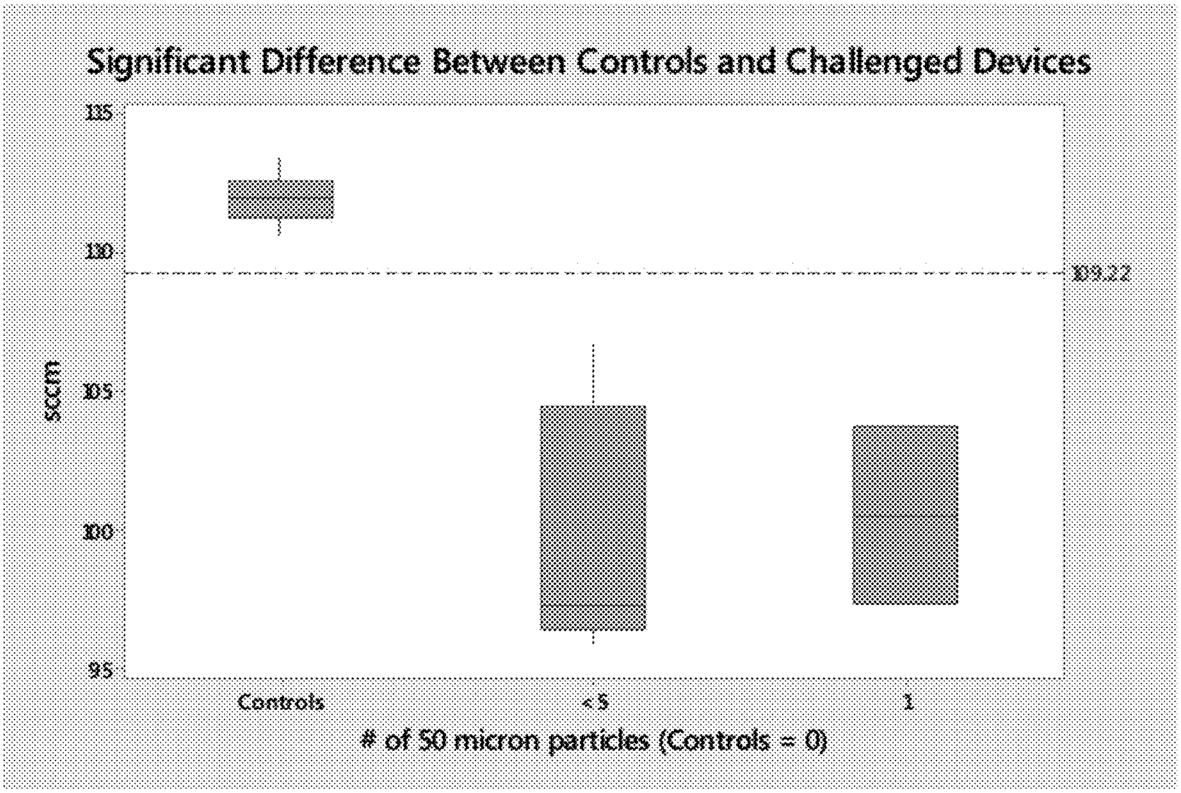
FIG. 5 is a plot showing the sccm of devices containing 5 or fewer, or a single 50-micron particle, and control devices. Dashed horizontal line represents the test acceptance criteria of 109.22 for the device.
Figure 6:
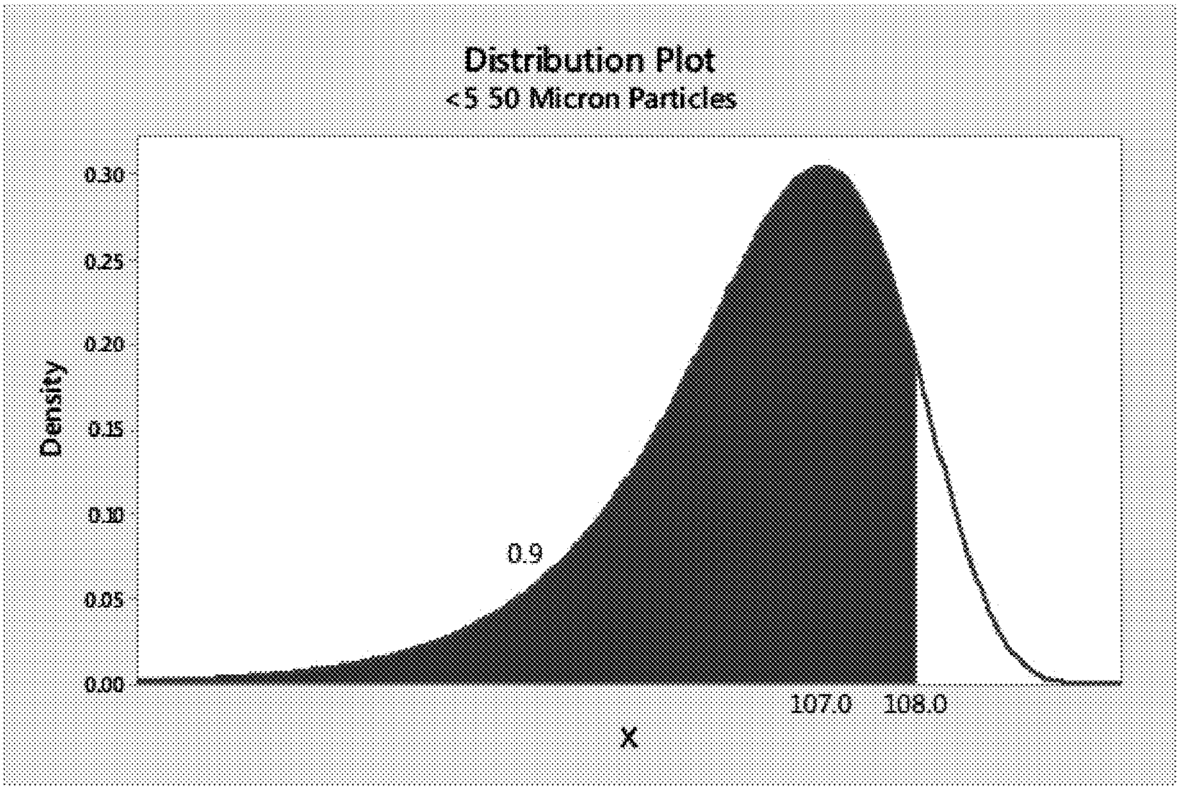
FIG. 6 are probability distribution plots of samples containing less than 5 particles prior to (Top), and after (Bottom) adding in system error. With system error, the test acceptance criteria approximates 95/99.8.
Figure 6:
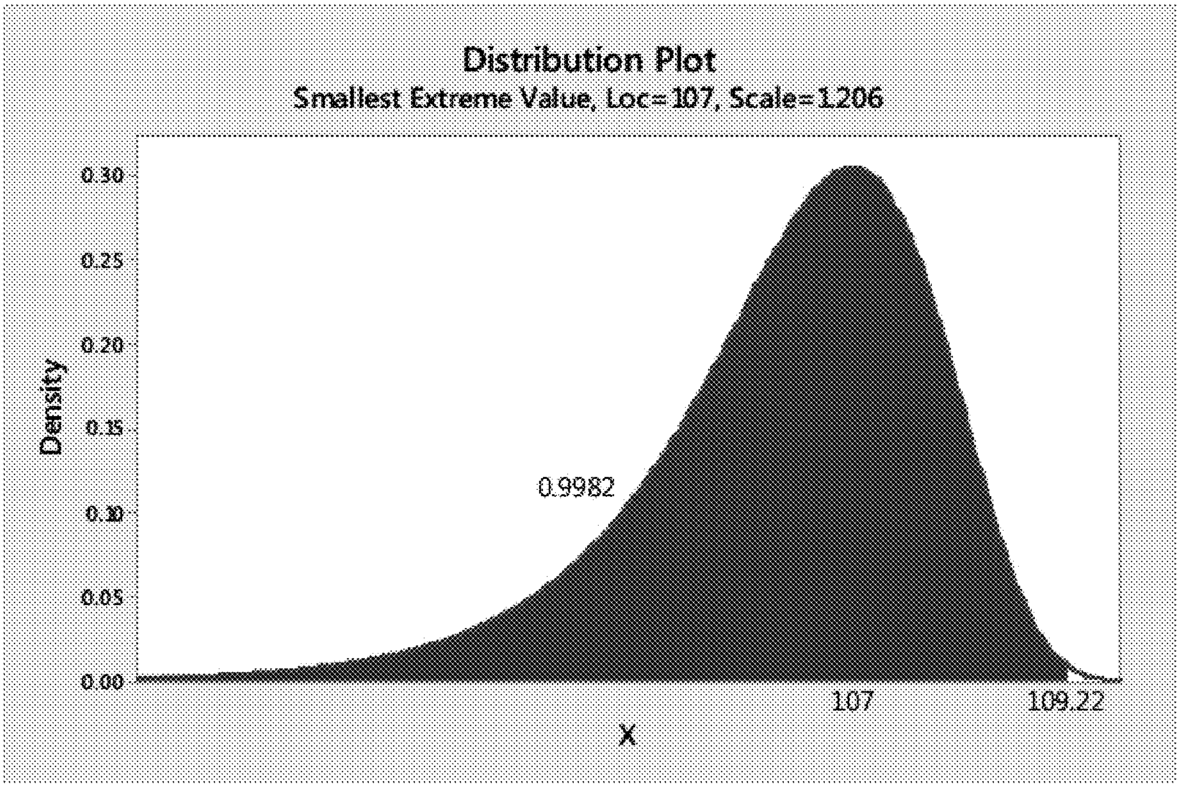

As seen in FIG. 5, both the <5 and 1 particle devices provided mass flow readings that were considerably lower than the 109.22 sccm defined acceptance criteria. In process, this would result in these devices failing the lumen inspection test and being rejected from further use. Applying a Probability Distribution Plot to the <5 micron particle data, the test acceptance criteria of 109.22 (95/90+system error) approximates 95/99.82, providing an even greater safety factor and confidence (FIG. 6).

Defined test parameters for the Biosense Webster PentaRay EP catheter are shown in Table 1.

| | |
|---|---|
| Prefill | 50% |
| Fill | 3.00 s |
| Test | 3.00 s |
| Exhaust | 0.50 s |
| Relax | 5.00 s |
| Minimum Change in Mass Flow (PASS) All data above this limit will pass | 109.23 sccm |
| Maximum Change in Mass Flow (FAIL) All data below this limit will fail | 109.22 sccm |

Additional confidence in this test method is provided by the fact that those flow values are only slightly lower than that achieved by devices occluded by 50 micron particles. Devices containing single (or multiple) larger particles would also be rejected by the acceptance criteria developed from the 50 micron particle data.

Full validation of the test conditions and acceptance criteria will be completed using a statistically significant sample set. A Nested Gage R&R will be performed by multiple independent operators using devices occluded in a consistent manner, validating the test program defined herein. This validation will be executed and reported prior to the submission for 510(k) approval of the PentaRay catheter, and a similar test method and subsequent validation developed and implemented during the investigation of other catheters containing microlumens.

Example 2. Occlusion Testing Criteria for Reprocessed Abbott (St. Jude Medical) Advisor HD Grid Mapping Catheters Occlusion testing acceptance criteria were defined for reprocessed Abbott (St. Jude Medical) Advisor HD Grid mapping catheters using the CTS Sentinel Blackbelt (CTS) tester. Specifications of the device are shown in Table 2.

TABLE 2

| Item Number | Description | Usable Length (cm) | French Size | Curve | Spacing (mm) | Electrodes | System Compatibility |
|---|---|---|---|---|---|---|---|
| D-AVHD-DF16 | Reprocessed Advisor HD Grid Mapping Catheter, Sensor Enabled | 110 | 8F | DF | 3 | 16 | EnSite Velocity and EnSite Precision Cardiac Mapping Systems |

CONCLUSION

It is well understood that fewer large (»200 micron) particles are required to create a similar embolic injury as smaller particles (<100 micron). However, the exact size, shape, or quantity of particles necessary remain unknown. While the clinical relevance of a single small embolic particle has not been established here, or elsewhere, it is generally accepted that, in accordance with minimizing periprocedural patient risk, reducing the amount and size of particles on or in a catheter or other EP instrument is a common goal shared by all device manufacturers. Out of an abundance of caution, to provide a considerable safety factor for all manufactured devices to be inspected, 50 microns was selected as the clinically relevant particle size to be used to define acceptance criteria.

This study was designed to develop a test method capable of identifying catheters with lumens containing unacceptable amounts of potentially embolic particles. During this process, it was important to investigate the scale and sensitivity of the test instrument, and then set the test acceptance criteria to an appropriately safe and statistically justifiable value. Production devices will encounter the same conservative test as part of an in-process inspection step, rejecting any that are tested to or below the acceptance criteria of 109.22.

Results from a previous study showed that this system is also capable of identifying devices occluded by single larger (200 micron) particle, with flow readings near 104 sccm.

The CTS Sentinel Blackbelt Mass Flow Tester conducts leak and occlusion testing of small lumens. During mass flow testing, a device is initially charged to a set pressure and then the flow required to maintain that pressure is reported. Differences in this flow between the same type of device reflect restrictions in the lumen caused by occlusions, or other defects, that may negatively impact use of the device and may present potential patient risk. Flow-through devices of a different design or manufacturer may vary. However, provided the unimpeded flow of any subject device is within the performance range of the test system, the system can be adapted for inline inspection of production devices.

Per FDA recommendation, acceptance criteria required the identification of a single 50 um particle residing within the lumen of a reprocessed device and subsequent rejection of any device tested to retain such occlusions. Equipment capability, sensitivity, and test parameters were established in Example 1. The results of particulate identification testing, including the full test method validation, were recorded in Example 4.

Figure 7:
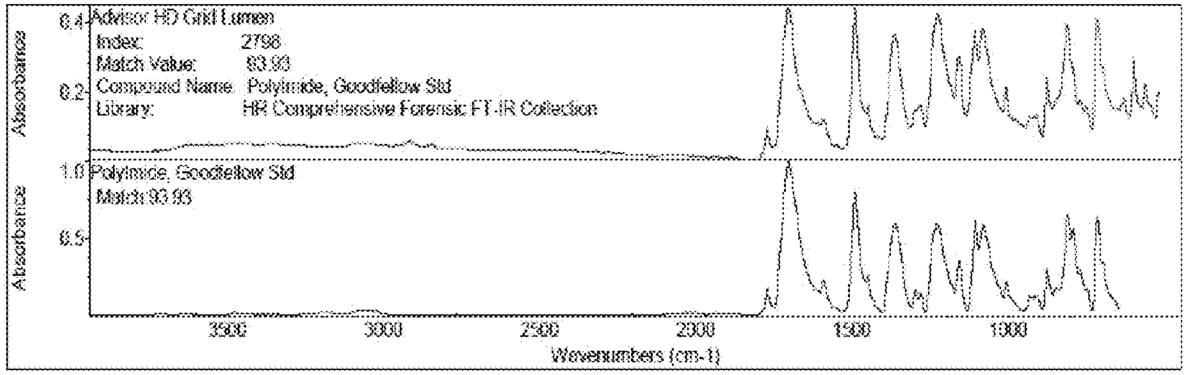
FIG. 7. FTIR Analysis of microlumens within the Advisor HD Grid and PentaRay catheters.
Figure 7:
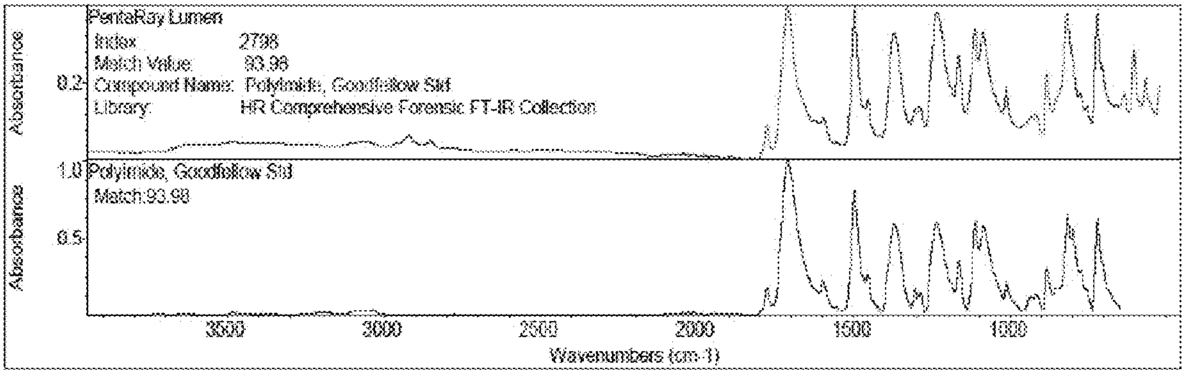

The Advisor HD Grid and PentaRay share similar design characteristics as shown by the Fourier-transform infrared spectroscopy (FTIR) obtained for both devices in FIG. 7. Both devices contain a polyimide microlumen that runs from proximal sideport tubing at the handle through the shaft exiting at the distal tip (FIG. 8). The Advisor HD Grid has a slightly larger lumen diameter (0.018" I.D.) than the PentaRay (0.012" I.D.), and the PentRay has a slightly longer usable length (115 cm) versus the Advisor HD Grid (110 cm). The Advisor HD Grid also has a perforated cap over the lumen at the distal tip, whereas the PentaRay terminates in an open lumen. All these properties affect the flow rate necessary to maintain the set pressure, which is why characterization of each subject device is required in the development of device-specific test acceptance criteria.

Understanding that flow characteristics are unique to each device, the data from the study conducted herein will be used to define acceptance criteria for the Advisor HD Grid. Flow Characterization and Occlusion.

Samples selected included sixty-eight (68) clinically-used and reprocessed devices and two (2) original manufacturer (OM) devices. On the CTS system, using a new program with no acceptance criteria, initial characterization of the two OM and fifty-eight of the reprocessed devices was performed to assess the non-occluded flow rate. Fifty-eight reprocessed devices were then prepared, inoculating a single 50 μm bead into the lumen at the proximal end and then incubated a minimum of 48 hours at 65° C. prior to testing (to ensure the evaporation of the bead buffer solution which might otherwise affect test results).

Ten (10) reprocessed devices were inoculated with the bead buffer solution alone (no particulate) to serve as carrier controls. Following incubation, the devices were analyzed on the CTS, recording a single flow measurement for each sample.

Results are shown in FIGS. 9A-C to FIG. 14. Data was analyzed in Minitab 18. At 95/95 confidence, the upper bound of the probability plot for the devices containing a particulate defines the acceptance criteria.

Based on these measurements, it was determined that acceptance criteria for the Advisor HD Grid device is 157.32 sccm. Advisor HD Grid devices that test at or below these measurements will FAIL. Devices that test above these measurements will PASS.

Example 3. Occlusion Testing Acceptance Criteria for Reprocessed St. Jude Medical BRK Transseptal Needles Using the CTS Sentinel Blackbelt (CTS) Tester Specifications of the device are shown in Table 3.

TABLE 3

| OEM Product | Device | OEM Product Code | Needle Gauge Size | Bevel Angle | Curve Type | Usable Length (cm) |
|---|---|---|---|---|---|---|
| St. Jude Medical BRK Transseptal Needles | Transseptal Needle | 407200 | 18 ga | 50° | BRK | 71 |
| | | 407201 | | | BRK-1 | 71 |
| | | 407205 | | | BRK | 89 |
| | | G407215 | | | BRK-1 | 89 |
| | | 407206 | | | BRK | 98 |
| | | 407207 | | | BRK-1 | 98 |
| St. Jude Medical BRK XS Transseptal Needles | | G407208 | | 30° | BRK XS | 71 |
| | | G407209 | | | BRK-1 XS | 71 |
| | | G407210 | | | BRK XS | 89 |
| | | G407216 | | | BRK-1 XS | 89 |
| | | G407211 | | | BRK XS | 98 |
| | | G407212 | | | BRK-1 XS | 98 |

Devices were reprocessed and inoculated with a single 50 μm bead into the lumen of OM and clinically-used, reprocessed devices. Devices were incubated a minimum of 48 hours at 65° C. prior to testing. On the CTS system, using a new program with no acceptance criteria, initial characterization of an OM, non-occluded device was conducted to establish the flow rate range for both 71 and 98 cm devices. Challenged devices were then analyzed and 5 measurements recorded for each sample. Each sample was tested five (5) times. The number of unique samples tested can be calculated by dividing the data points (N) shown by five (5). Data was analyzed in Minitab 18. A95/90 Confidence Interval is used to define the acceptance criteria for each needle. Results are shown in FIGS. 15A-C to FIG. 19.

Test program acceptance criteria is unique to the length of the needle and is defined as shown in Table 4.

TABLE 4

| Needle size (cm) | Flow rate acceptance criteria (sccm) |
|---|---|
| 71 | 175.8 |
| 89 | 161.1 |
| 98 | 154.3 |

Respective devices that test at or below these measurements will FAIL. Devices that test above these measurements will PASS.

Example 4. Detecting a Single 50 um Particle in Small Lumens

The purpose of this report is to provide documented evidence that the CTS Sentinel Blackbelt (CTS) tester using the small lumen occlusion test method and parameters defined in Example 1 is capable of reliably detecting a single 50 um occlusion in small lumens (similar to those found in the PentaRay family of products).

The study used the following subject device:

TABLE 5

| Device Scope | |
|---|---|
| Original Manufacturer (OM): | Biosense Webster |
| OM Description: | PentaRay Nav eco High-Density Mapping Catheter |
| OM Item Number(s): | See Table 2 below. |
| Device Used: | D128207, D128208, D128210, D128211 |

TABLE 6

| Item Numbers | | | | | | |
|---|---|---|---|---|---|---|
| Item Number | Description | Usable Length (cm) | French Size | Curve | Spacing (mm) | Electrodes |
| D128207 | PentaRay Nav eco High-Density | 115 | 7F | F | 4-4-4 | 20 |
| D128208 | PentaRay Nav eco High-Density | 115 | 7F | F | 2-6-2 | 20 |
| D128210 | PentaRay Nav eco High-Density | 115 | 7F | D | 4-4-4 | 20 |
| D128211 | PentaRay Nav eco High-Density | 115 | 7F | D | 2-6-2 | 20 |

Equipment List (as Below or Equivalent/Similar)

6.1 1 ml 28G×½" disposable syringe (10049962)
6.2 50 ml Conical (43237-2)
6.3 Bangs Bead Solution with 0.1% surfactant (SOLN1)
6.4 Polyvinylpyrrolidone (PVP40-50G)
6.5 50 um Particle Size-Standard Solution (64190-15)
6.6 4-2500× Compound Microscope (B120C-E1)
6.7 1.3MP Digital Camera (MD130)
6.8 0-6× Celestron Microscope (44308)
6.9 Particle Trap Plates
6.10 Single Channel Pipettors & Disposable Tips
6.11 CTS Sentinel Blackbelt with Mass Flow Sensor
6.12 PentaRay Occlusion Test Fixture (T-0056)

Sample Device Collection and Processing:

Devices that were used for this study include sixty-eight (68) clinically used (natively soiled) reprocessed PentaRay devices received from various collection sites covering all item numbers listing in the scope (Table 5). Twenty-Nine (29) devices were inoculated with a single 50 urn particle as described in Example 1. Twenty-Nine (29) devices were left unchallenged following reprocessing. The remaining ten (10) devices were challenged with bead buffer alone (SHAM).

Figure 20:
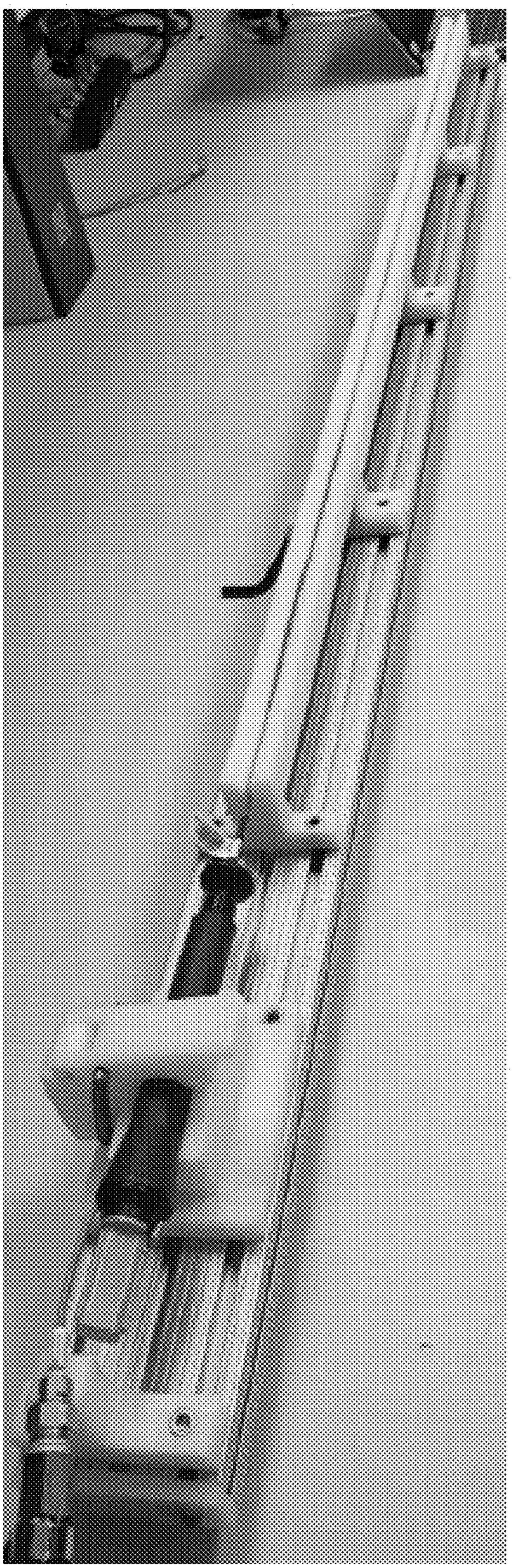
FIG. 20. Image of a test fixture.
Figure 21:
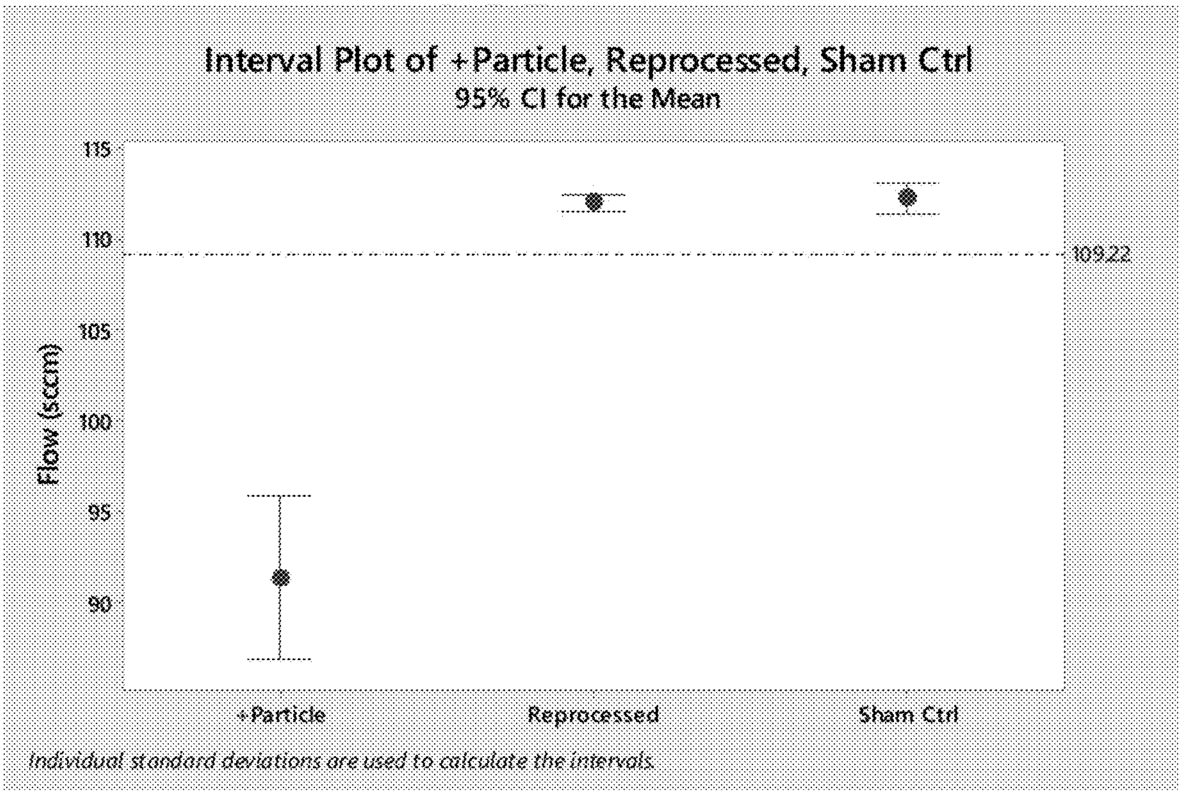
FIG. 21. Mass Flow readings for devices challenged with a single 50 urn particle, reprocessed (unchallenged devices), and Sham Control devices (challenged with bead buffer alone). 109.22 sccm was defined as the test acceptance criteria during test method development (Example 1).

A test fixture (T-0056; FIG. 20) was utilized to straighten each device shaft during testing, reducing variability introduced by random positioning. The distal tip of the device was shielded with an open-bottom conical tube positioned against the particle trap plate, which allowed the recovery of a particle exhausted from the lumen during testing.

Inoculation, syringe, and lumen flushing images were recorded using 4-2500× magnification on an AmScope microscope fitted with a 1.3MP digital zoom capable camera. Particle traps were analyzed and images recorded using 0-60× magnification provided by a Celestron microscope.

Acceptance Criteria:

TEST PROGRAM acceptance criteria are defined to be 109.22 (Standard Cubic Centimeters per Minute) sccm, as documented in Example 1.

Mass Flow>109.22 sccm=PASS

Mass Flow≤109.22 sccm=FAIL

Known Good devices PASS, known bad devices (challenged with a single 50 μm particle) FAIL, and the study shall achieve 95/90 confidence.

Deviation:

Data was analyzed in Minitab18 to 95% confidence.

Results:

Results are shown in FIG. 21 to FIG. 25.

Discussion

Figure 22:
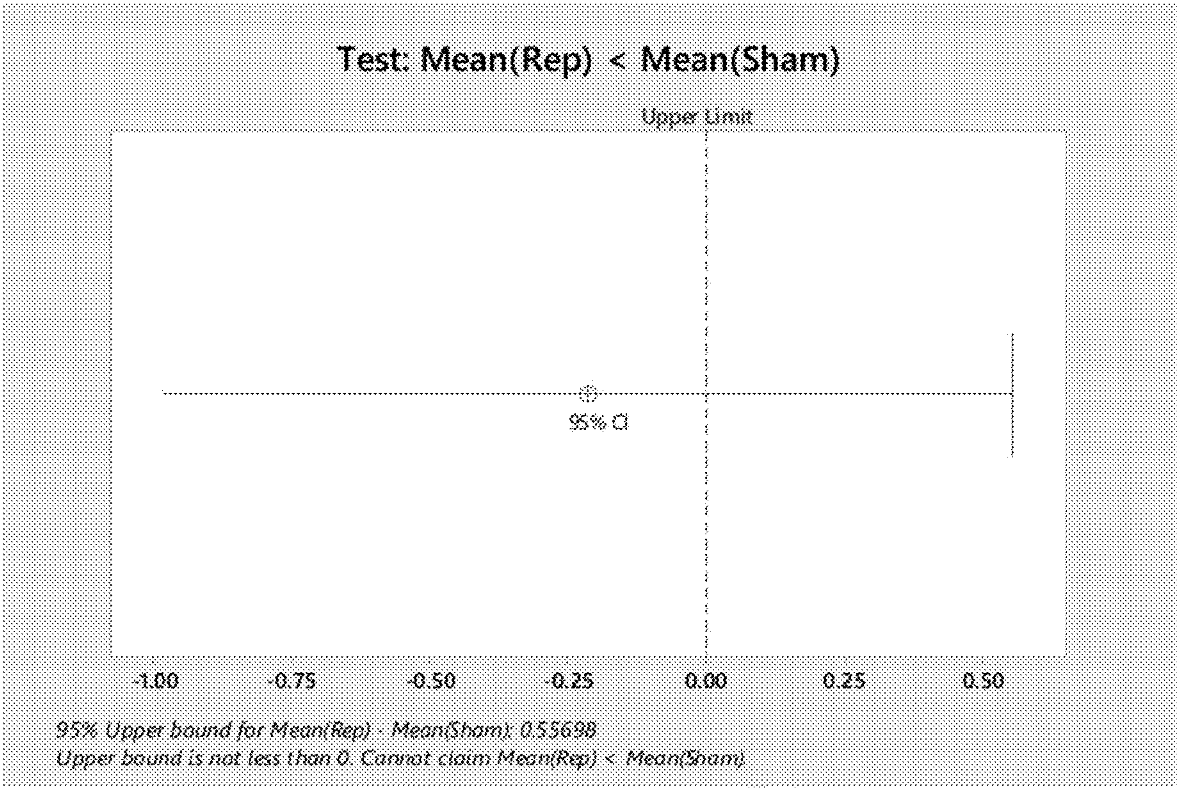
FIG. 22. No statistical difference in mass flow readings noted between unchallenged reprocessed device and sham control (challenged with bead buffer only) devices.
Figure 23:
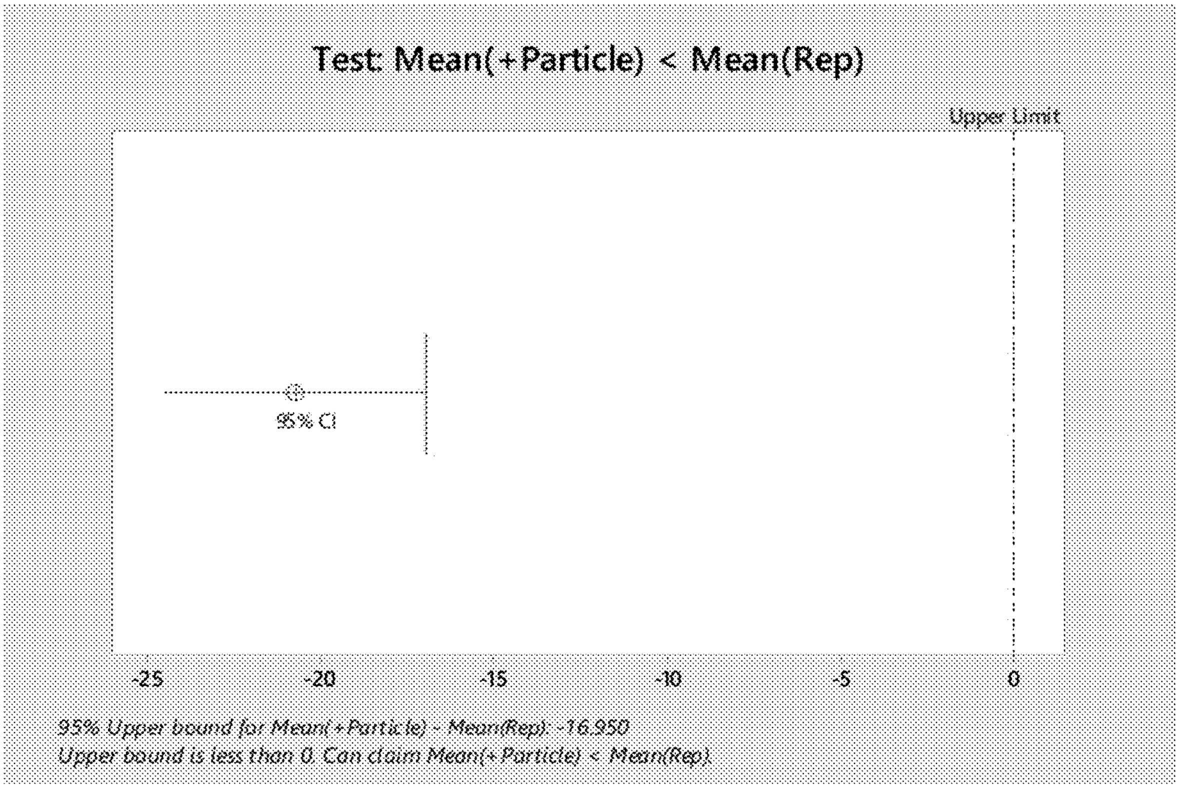
FIG. 23. A statistical difference noted in mass flow readings between unchallenged reprocessed devices and those challenged with a single 50 urn particle.

As observed in the interval plot (FIG. 21), all mass flow data for the unchallenged reprocessed samples and sham control sets are above the test acceptance limit, while the challenged device data points are well below the acceptance limit. There was no statistically significant difference between mass flow readings among the unchallenged reprocessed and sham (challenged with bead buffer alone) sample sets (FIG. 22). However, there was a remarkable difference between unchallenged reprocessed and challenged sample sets (FIG. 23).

Figure 24:
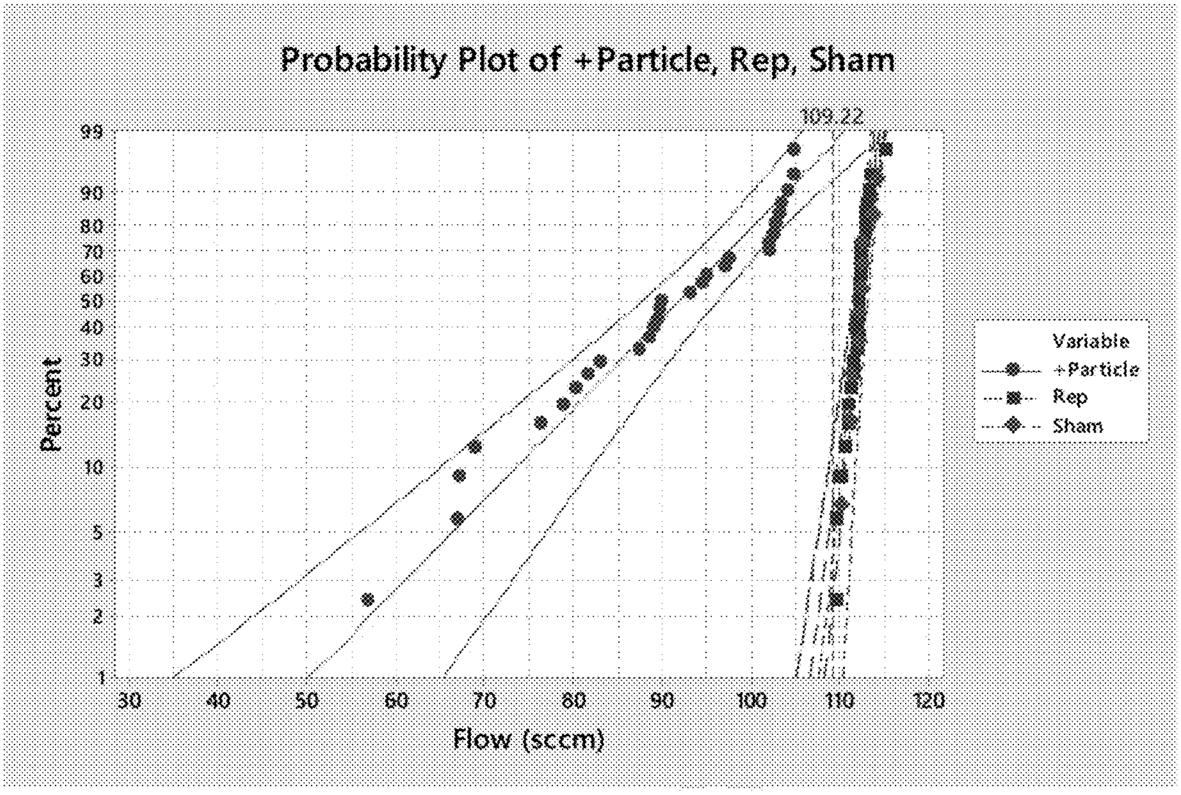
FIG. 24. A probability plot suggests that the acceptance criterion (109.22 sccm) is more conservative than that reported at the 95%/90% Upper Bound (107.66 sccm) for challenged devices. All control and unchallenged samples record mass flow readings higher than the acceptance criterion, while all challenged devices record readings well below the acceptance criterion.
Figure 25:
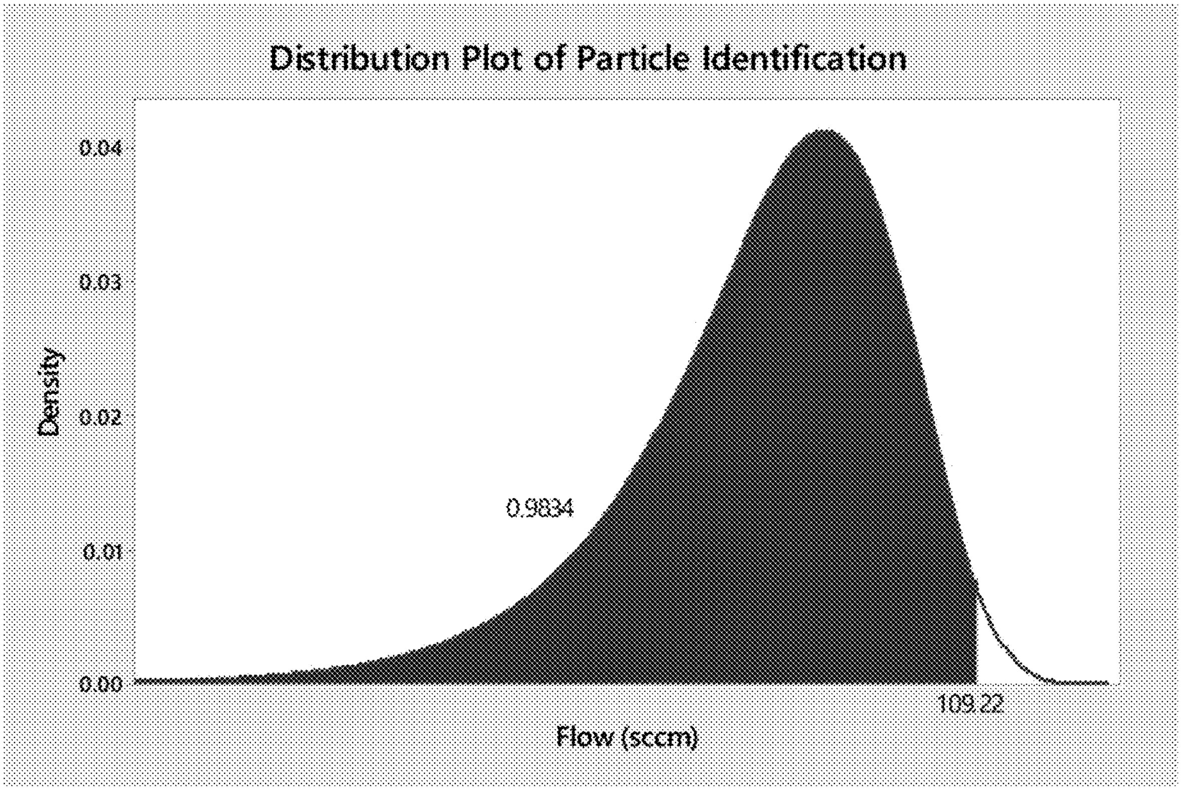
FIG. 25. A probability plot suggests that production devices containing a single 50 urn occluding particle will test at a 95%/98.3% confidence interval when applying the following acceptance criterion of Mass Flow 109.22 sccm=FAIL.

The 95%/90% upper bound of the probability plot for the challenged device data recommends a test acceptance limit of 107.66 sccm (FIG. 24). Retaining the 109.22 sccm test limit defined during test method development exceeds 95%/98% (FIG. 25). This further suggests that the defined test acceptance limit is quite conservative and includes a considerable safety factor.

Figure 26:
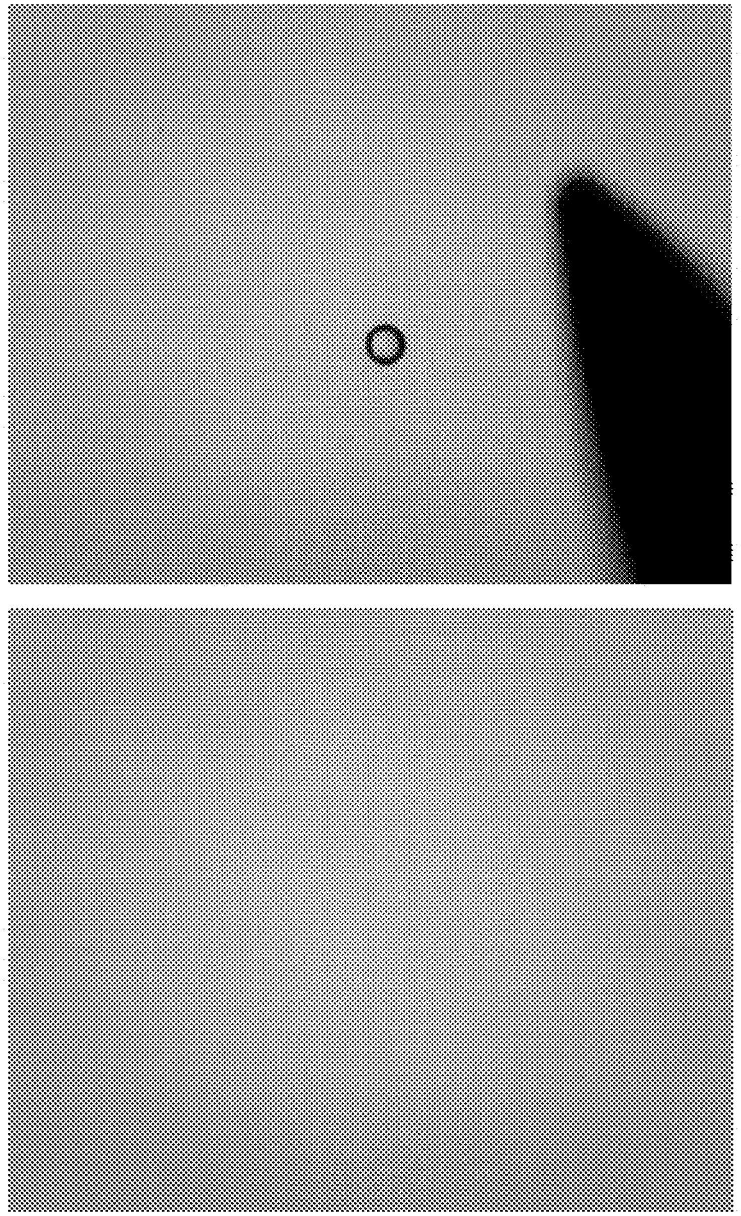
FIG. 26. Images of an isolated particle prior to testing (top) and flush fluid after testing (bottom).

Magnified images taken both prior to and following inoculation and testing (Example in FIG. 26) provide evidence that test conditions involved a single particle inoculated within the lumen of challenged devices. It is of interest that devices that exhausted the particle during testing (where the particle was observed in the particle trap following testing) experienced a measurably higher flow rate than those that retained the particle (as evidenced by the absence of a particle on the particle trap, but its presence in the lumen flush fluid). The objective of this study was to develop an inline inspection test capable of detecting and rejecting devices that contain a single 50 um particle within the lumen of a reprocessed device.

CONCLUSION

This study was conducted at a 95%/90% confidence interval to validate the acceptance criterion for the small lumen occlusion test. This confidence interval required 29 of 29 challenged samples to FAIL (read at or lower than 109.22 sccm) and 29 of 29 unchallenged reprocessed samples to PASS (read higher than 109.22 sccm). This was achieved, signifying that the CTS mass flow tester is capable of reliably detecting occlusions as small as a single 50 um particle in lumens of reprocessed subject devices. It also confirms that this test program is capable of reliably rejecting devices that contain such occlusions.

REFERENCES

1. Horowitz, L. N.; Kay, H. R.; Kutalek, S. P.; Discigil, K. F.; Webb, C. R.; Greenspan, A. M.; Spielman, S. R. Journal of the American College of Cardiology 1987, 9 (6), 1261-1268.
2. Haghjoo, M.; Vasheghani-Farahani, A.; Shafiee, A.; Akbarzadeh, M.; Bahrololoumi-Bafruee, N.; Alizadeh- Diz, A.; Emkanjoo, Z.; Fazelifar, A.; Bakhshandeh, H. Research in Cardiovascular Medicine 2018, 7 (1), 20.
3. Electrophysiological Studies. Hopkins medicine test_procedures cardiovascular electrophysiologic al_studies_92, p07971 (accessed Dec. 18, 2018).
4. USP<788> PARTICULATE MATTER IN INJECTIONS, The United States Pharmacopeial Convention, 2018
5. Langille, S. PDA Journal of Pharmaceutical Science and Technology 2013, 67, 186-200.
6. Puntis, J.; Wilkins, K.; Ball, P.; Rushton, D.; Booth, I. Archives of Disease in Childhood 1992, 67, 1475-1477.
7. Mettler, F.; Guiberteau, M. Essentials of nuclear medicine imaging; Elsevier Saunders: Philadelphia, 2012.
8. AAMI TIR42:2010, Evaluation of Particulates Associated With Vascular Medical Devices
9. Food and Drug Administration (FDA). Coronary, Peripheral, and Neurovascular Guidewires—Performance Tests and Recommended Labeleing; 2018.
10. Haines, D.; Stewart, M.; Ahlberg, S.; Barka, N.; Condie, C.; Fiedler, G.; Kirchhof, N.; Halimi, F.; Deneke, T. Circulation: Arrhythmia and Electrophysiology 2013, 6, 16-22.
11. Haines, D.; Stewart, M.; Barka, N.; Kirchhof, N.; Lentz, L.; Reinking, N.; Urban, J.; Halimi, F.; Deneke, T.; Kanal, E. Circulation: Arrhythmia and Electrophysiology 2013, 6, 23-30.
12. Rapp, J.; Pan, X.; Sharp, F.; Shah, D.; Wille, G.; Velez, P.; Troyer, A.; Higashida, R.; Saloner, D. Journal of Vascular Surgery 2000, 32, 68-76.
13. Reina-De La Torre, F.; Rodriguez-Baeza, A.; Sahuquillo-Barris, J. The Anatomical Record 1998, 251, 87-96.

What is claimed is:

1. A method of detecting a change in a lumen property of a lumen device, the method comprising:

a. obtaining or having obtained a flow measurement for the device to be inspected; and b. comparing the flow measurement in the device to an upper test limit of flow obtained for an occluded representative device with a defined level of occlusion;

wherein the lumen property of the device to be inspected is determined to be changed if the flow measurement for the device to be inspected is equal to or lower than the upper test limit of flow, and the lumen property of the device to be inspected is determined to be unchanged if the flow measurement for the device to be inspected is greater than the upper test limit of flow.

2. The method of claim 1, further comprising determining the upper test limit of flow of the occluded representative device.

3. The method of claim 2, wherein determining the upper test limit of flow includes:

a. obtaining or having obtained a flow measurement for the occluded representative device, wherein the defined level of occlusion includes a defined number of one or more occluding particles; and b. calculating the upper test limit of flow for the occluded representative device.

4. The method of claim 1, wherein the occluded representative device is an unused originally manufactured device (OM), a used OM device, an unused reprocessed device, or a used reprocessed device.

5. The method of claim 1, wherein the change in the lumen property comprises a change in dimensions of the lumen, a change in material of the lumen, a change in device-specific parts attached along the lumen, or any combination thereof.

6. The method of claim 5, wherein the change in material of the lumen comprises a change in material used to manufacture of the lumen by an original manufacturer, a change in material caused by intended alteration of the device, a defect caused during manufacture, a defect caused during shipping and handling of the device, a defect caused during use of the device, a change in physical characteristics of a lumen resulting from use of the device, or any combination thereof.

7. The method of claim 5, wherein the change in the dimensions of the lumen comprises an occlusion in the lumen, a change in an inner diameter and shape, tube curvature, tube length, a damaged lumen, a manufacturing defect, a new coating, and/or a chipped coating.

8. The method of claim 1, wherein the change in the lumen property of the device to be inspected occurred before manufacture, during manufacture, during shipping and handling, during use, after use but before re-processing, during reprocessing, after reprocessing or any combination thereof.

* * * * *